US011355226B2

United States Patent
Härmä

(10) Patent No.: US 11,355,226 B2
(45) Date of Patent: Jun. 7, 2022

(54) AMBULATORY PATH GEOMETRIC EVALUATION

(71) Applicant: KONINKLIJKE PHILIPS N.V., Eindhoven (NL)

(72) Inventor: Aki Sakari Härmä, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 792 days.

(21) Appl. No.: 16/323,297

(22) PCT Filed: Aug. 4, 2017

(86) PCT No.: PCT/EP2017/069872
§ 371 (c)(1),
(2) Date: Feb. 5, 2019

(87) PCT Pub. No.: WO2018/024908
PCT Pub. Date: Feb. 8, 2018

(65) Prior Publication Data
US 2021/0335474 A1    Oct. 28, 2021

Related U.S. Application Data

(60) Provisional application No. 62/371,249, filed on Aug. 5, 2016.

(51) Int. Cl.
*G01C 21/20*     (2006.01)
*G16H 20/30*     (2018.01)
(Continued)

(52) U.S. Cl.
CPC ............ *G16H 20/30* (2018.01); *A61B 5/1112* (2013.01); *A61B 5/1118* (2013.01); *A61B 5/165* (2013.01);
(Continued)

(58) Field of Classification Search
CPC ........ G16H 20/30; G16H 50/70; G06V 40/23; A61B 5/1112; A61B 5/1118; A61B 5/165; A61B 5/681; A61B 5/7264; A61B 5/74; A61B 2503/12; A61B 2562/0219; A63B 24/0006; A63B 24/0021; A63B 24/0087; A63B 2024/0025; A63B 2024/0081; A63B 2024/0093; G01C 22/006
See application file for complete search history.

(56) References Cited

U.S. PATENT DOCUMENTS

2011/0167079 A1   7/2011   Haridasan
2014/0176422 A1   6/2014   Brumback
(Continued)

FOREIGN PATENT DOCUMENTS

WO   WO2016079719 A1   5/2016

OTHER PUBLICATIONS

PCT International Search Report, International application No. PCT/EP2017/069872, dated Nov. 14, 2017.
(Continued)

*Primary Examiner* — Mohamed Charioui
*Assistant Examiner* — Christine Y Liao
(74) *Attorney, Agent, or Firm* — Michael W. Haas

(57) ABSTRACT

In an embodiment, an apparatus (16) is presented that classifies device-sensed movement along a path based on a score that characterizes a geometrical property of the movement.

18 Claims, 8 Drawing Sheets

(51) Int. Cl.
*A61B 5/11* (2006.01)
*A61B 5/16* (2006.01)
*A63B 24/00* (2006.01)
*A61B 5/00* (2006.01)
*G16H 50/70* (2018.01)
*G06V 40/20* (2022.01)
*G01C 22/00* (2006.01)

(52) U.S. Cl.
CPC ............ *A61B 5/681* (2013.01); *A61B 5/7264* (2013.01); *A61B 5/74* (2013.01); *A63B 24/0006* (2013.01); *A63B 24/0021* (2013.01); *A63B 24/0087* (2013.01); *G06V 40/23* (2022.01); *G16H 50/70* (2018.01); *A61B 2503/12* (2013.01); *A61B 2562/0219* (2013.01); *A63B 2024/0025* (2013.01); *A63B 2024/0081* (2013.01); *A63B 2024/0093* (2013.01); *G01C 22/006* (2013.01)

(56) References Cited

U.S. PATENT DOCUMENTS

| | | | |
|---|---|---|---|
| 2015/0204676 A1* | 7/2015 | Zhang | G01S 5/0263 |
| | | | 701/410 |
| 2015/0335291 A1 | 11/2015 | Saadi | |
| 2015/0338236 A1 | 11/2015 | Hoffman | |
| 2018/0344215 A1* | 12/2018 | Ohnemus | A63F 13/798 |

OTHER PUBLICATIONS

Observations on the PCT International Search Report and the Written Opinion of International Application No. PCT/EP2017/069872, dated Nov. 7, 2018.

Dill J. et al., "Bicycling for Transportation and Health: The Role of Infrastructure", Journal of Public Health Policy (2009) 30, S95-S110.

Griffin P. et al., "Where does Bicycling for Health Happen? Analysing Volunteered Geographic Information through Place and Plexus", Journal of Transport & Health, vol. 2, Issue 2, Jun. 2015, pp. 238-24.

* cited by examiner

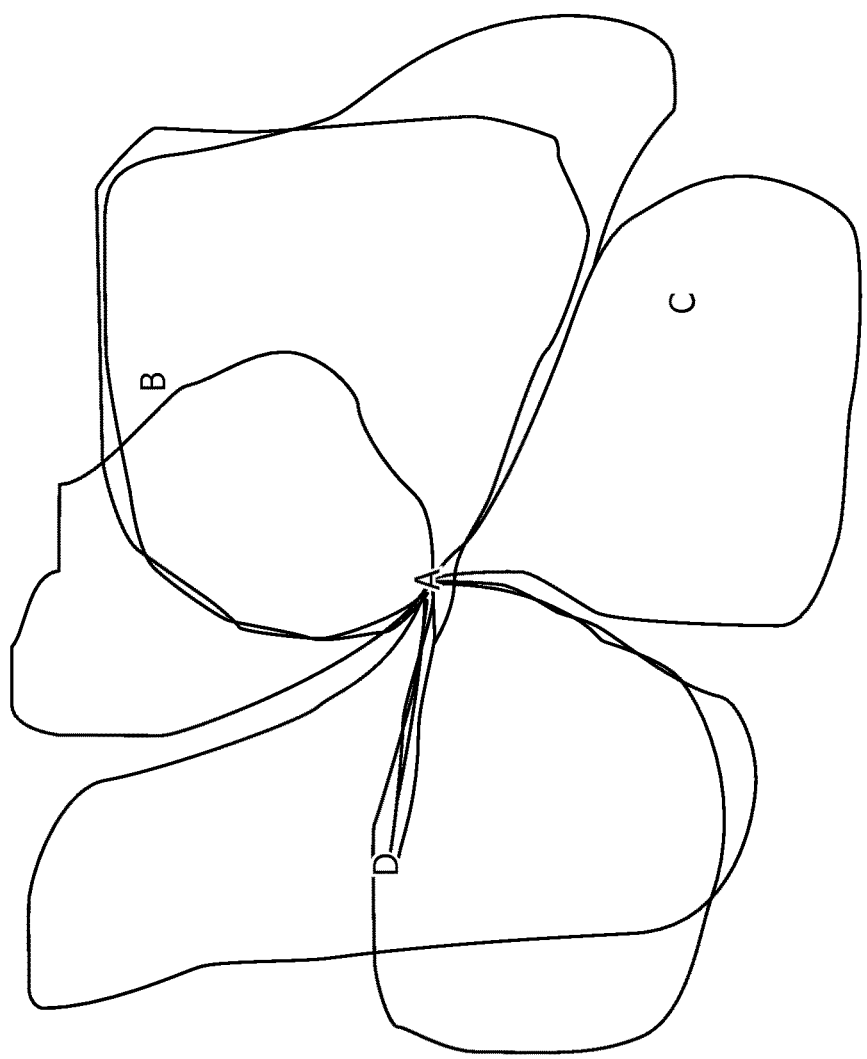
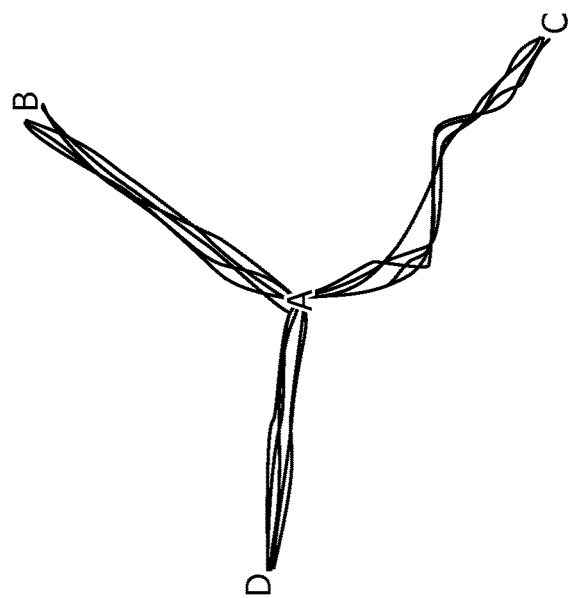
FIG. 1B
FIG. 1A

AMBULATORY PATH GEOMETRIC EVALUATION

CROSS-REFERENCE TO RELATED APPLICATIONS

This patent application claims the priority benefit under 35 U.S.C. § 371 of international patent application no. PCT/EP2017/069872, filed Aug. 4, 2017, which claims the priority benefit under 35 U.S.C. § 119(e) of U.S. Provisional Application No. 62/371,249 filed on Aug. 5, 2016, the contents of which are herein incorporated by reference.

FIELD OF THE INVENTION

The present invention is generally related to context-based activity monitoring.

BACKGROUND OF THE INVENTION

Activity of a user can be tracked, but providing context-suitable messaging for a particular activity is very difficult. For example, a user may walk to simply buy groceries at a store or may walk for the purpose of increasing exercise. The data from wearable sensor devices can track the activity of the user but messaging often lacks a comprehensive semantic frame of reference or context, or is based on inferences that may be erroneous based on the monitored data. For example, a health service may provide messaging to a user that influences the user to become more active and take a walk. If the service, based on feedback from an activity tracker, determines the user has taken a certain number of steps, it is not known to the service whether the steps were gained during a walk with a purpose to increase activity for some other reason that required the user to walk. Suitable messaging should be based on accurate contextual intelligence from the activity monitoring device. Jennifer Dill's, "Bicycling for Transportation and Health: The Role of Infrastructure" (Journal of Public Health, 2009), describes a survey that collects GPS and user questionnaire data on bicycling behavior and determines its relationship to health and public infrastructure (see, e.g., Abstract). The survey found differences in travel length between exercise related bicycling trips and work related trips (see, e.g., page 6) and examined utilitarian trips separately from exercise trips, suggesting that cyclists may have different route preferences for exercise trips, such as spending more time on a bike path as opposed to bike lanes (see, e.g., page 7).

SUMMARY OF THE INVENTION

One object of the present invention is to provide an alternative to existing, computationally-intensive and/or information-deficient, contextual-based activity monitoring. To better address such concerns, in a first aspect of the invention, an apparatus is presented that classifies device-sensed movement along a path based on a score that characterizes a geometrical property of the movement. The invention addresses a problem of often deciphering numerous data points and inferring from those points a context for an activity to enable helpful feedback to a user by implementing a less computationally intensive, alternative scheme, or supplementing existing schemes to provide additional accuracy in providing contextual intelligence based on a computed score from ambulatory path geometry.

In an embodiment, an apparatus, comprises: a user interface; plural sensors, wherein at least one of the sensors monitors movement of the apparatus; a memory comprising: a data structure having plural entries that store respective contextual messages; and application software; and at least one processor configured to execute the application software to: receive signals encoded with data from one or more of the plural sensors during movement of the apparatus along a path; determine from the data plural parameters, the plural parameters comprising a length of the path and one of an area or a normalized correlation coefficient; compute a score from the determination of the plural parameters, the score characterizing a geometrical property of the movement along the path; classify the movement along the path based on the score; access one of the plural entries based on the classification; and cause a presentation of one of the contextual messages of the accessed one of the plural entries via the user interface. For instance, the apparatus may comprise a wearable device, such as an activity tracker that is attached to a user (e.g., secured to, or integrated with, clothing worn by the user, or worn around a limb or torso of the user, such as a wrist-worn device). The apparatus may be a handheld, portable device, such as a smartphone, personal digital assistant, or other communications/computing device that receives the sensor data from the wearable device or integrates all or a portion of the sensors. At least a portion of the sensors may detect movement. For instance, one or more of the sensors may be a location detecting or determining device, including a global navigation satellite systems (GNSS) receiver/transceiver and/or a motion tracking/sensing device, including an accelerometer (e.g., single axis, multi-axis) and/or gyroscope, etc. Some devices may incorporate both types of sensors. Additional sensors may include sensors for measuring physiological and/or behavioral parameters, including heart rate, skin conductance, blood pressure, respiration rate, among others. The data resulting from operation of the movement sensing sensors is used to determine plural parameters including a path length and either an area or a normalized coefficient, and based on the plural parameters, determine a score that characterized a geometrical property of movement along the path. When used as an alternative to existing schemes that use a multitude of data to provide contextual intelligence, the apparatus may classify the activity (e.g., determine a purpose of the movement along the path, including whether utilitarian or health-related) using fewer computational resources (e.g., less sensor data to monitor), improving the efficiency of the computational resources. Also, it is noted that the apparatus need not necessarily require an external service for map and business/place information, which is often unavailable outside of urban areas and/or may be costly to use (e.g., due to roaming charges). When used as a supplement to existing context determining schemes, the apparatus may improve the overall accuracy of the contextual intelligence, enabling the provision of contextual messages (e.g., coaching and/or motivational messages) that are more suited to the activity engaged in by the user.

In an embodiment, the processor is configured to execute the application software to: compute the score based on a ratio of the area and the square of the length; and classify the movement as either utilitarian or health-related, the classification based on comparing the score with a predetermined value. Again, the ratio of the area and a square of the length may be based entirely on data from the motion sensing sensors, reducing or eliminating the need for further computational resources when compared to existing systems, and enabling an efficient and quick approach to determining the contextual message for provision to a user. When supplementing existing systems, providing improved accuracy to the derived contextual intelligence.

In an embodiment, the processor is further configured to execute the application software to track instances of repeated movement of the apparatus along a particular path, the processor further configured to execute the application software to determine that the repeated movement corresponds to recurring healthy behavior, the processor further configured to execute the application software to perform one or more of the following: cause presentation of a contextual message that encourages the user to perform the healthy behavior more often; and cause presentation of a contextual message that informs the user about a contribution of the healthy behavior to one or a combination of health behavior targets or predicted physiological benefits. The apparatus tracks and encourages healthy behavior while providing the user with a point of reference of progress towards, or status relative to, various user or institutional targets, further providing real-time and useful coaching.

In an embodiment, the processor is configured to execute the application software to cause presentation of a contextual message that encourages a user to increase activity, the contextual message inherently intended to increase the score. In effect, the apparatus provides tips in real time to a user to improve or encourage healthy behavior, such as by increasing the length and/or area of the path traversed by the user when the opportunity to do so arises.

In an embodiment, the processor is further configured to execute the application software to, based further on at least the score: determine one or more supplemental paths; access one of the plural entries for one of the contextual messages associated with the one or more supplemental paths; and present via the user interface the one of the accessed contextual messages associated with the one or more supplemental paths. For a health program or service, it is important to discover potentially healthy habits the user already has and try to possibly increase their occurrence and intensity. For example, if the user sometimes takes a walk around a park or bicycle trip, it is beneficial that the health program can detect this activity, properly classify the activity, and try to encourage the user to increase similar activity. However, it is difficult to detect such activities and separate them from other recurring activities such as going to a local supermarket in the evenings. The apparatus, based on the computation of the score from the movement sensing data, can distinguish utilitarian from health-related activities, and when determined to be a health-related activity, determine and suggest to the user supplemental paths that may lengthen the distance the user runs or cycles and/or increases the duration and/or frequency of the health-related activity, bolstering the health of the user and/or advancing the progress in achieving his or her goals. As one example, the apparatus may suggest to the user that he or she perform the activity more often (e.g., 3-4 times per week instead of once per week).

In an embodiment, the at least one of the sensors comprises a location tracking device, and wherein, prior to the determination of the plural parameters, the processor is further configured to execute the application software to: identify recurring locations for the apparatus; sample a plurality of coordinates using the location tracking device for a plurality of paths associated with the movement of the apparatus to and from the recurring locations; and determine a type of activity associated with the movement of the apparatus for each of the plurality of paths. As set forth previously, it is difficult to distinguish the purpose of the activity (e.g., utilitarian or health-related), so by tracking the ingress/egress associated with one or more locations (e.g., by frequency), the apparatus can restrict computations of the score to paths taken for health-related purposes only, reducing extraneous computations, which is particularly important for power-conscious, battery-operated or alternative-energy based devices.

In an embodiment, the processor is further configured to execute the application software to restrict the determination of the plural parameters to apparatus movement where there is an associated threshold level of sensed physical activity of a user received from the plural sensors. Again, when used as an alternative to existing systems, the latter which may persistently process numerous types of data, the apparatus conserves on computational resources, preserving power and operating more efficiently.

In an embodiment, the processor is further configured to: determine a cognitive state of a user based on the score; access one of the plural entries for one of the contextual messages based on the determination of the cognitive state; and present the one of the accessed contextual messages that is based on the determination of the cognitive state via the user interface. The improvement in intelligence gathering may assist in the suitability of the message, enhancing/improving the cognitive state of the user.

In an embodiment, the at least one of the sensors comprises a motion tracking device, and wherein, prior to the determination of the plural parameters, the processor is further configured to execute the application software to: identify a pattern of recurring locations for the apparatus; identify a pattern of movement of the apparatus along a plurality of paths to and from the recurring locations; determine a type of activity associated with the movement of the apparatus for each of a plurality of paths; and restrict the determination of the plural parameters to apparatus movement where there is an associated threshold level of sensed physical activity of a user received from the plural sensors. As set forth above, the motion tracking device may be an inertial type sensing device, including a gyroscope and/or accelerometer. The receipt of motion tracking data enables the apparatus to determine patterns of ingress/egress and other behaviors without the need for GNSS hardware/software or the associated coordinate data, reducing complexity and/or cost of the apparatus. Also, by not requiring the apparatus to access external location information services (e.g., for GPS functionality), power consumption and/or cost of wireless communication functionality of the apparatus is conserved and/or reduced.

In an embodiment, processor is further configured to execute the application software to determine the plural parameters, wherein the plural parameters comprises the equivalent to the area, by: determining a normalized correlation coefficient based on motion data from the motion tracking device and additional data from the plural sensors for movement of the apparatus to and from one of the identified recurring locations, the normalized correlation coefficient characterizing a similarity of the paths to and from the identified recurring locations; and computing the score based on a combination of the normalized correlation coefficient and the length. The use of a normalized correlation coefficient, in conjunction with the motion tracking device, enables the aforementioned benefits of using a score-based mechanism to classify the activity and provide helpful feedback without requiring the complexities and/or cost of GNSS devices.

In an embodiment, a system, comprising: a memory comprising: a data structure having plural entries that store respective contextual messages; and application software; and a processor configured to execute the application software to: receive signals encoded with data; determine from the data plural parameters, the plural parameters comprising a length of a path and one of an area or a normalized correlation coefficient; compute a score from the determination of the plural parameters, the score characterizing a geometrical property of device movement along the path; classify the movement along the path based on the score; access one of the plural entries based on the classification; and provide one of the contextual messages of the accessed one of the plural entries. The system likewise contemplates the benefits and/or advantages of the apparatus without the use of on-board sensors, while also enabling an off-loading of computational processes, which conserves power of the wearable device and/or portable device.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

FIGS. 1A and 1B are schematic diagrams that illustrate example paths derived from data points associated with movement of a user for activities during the week and weekend, respectively, in accordance with an embodiment of the invention.

DETAILED DESCRIPTION OF EMBODIMENTS

Figure 2:
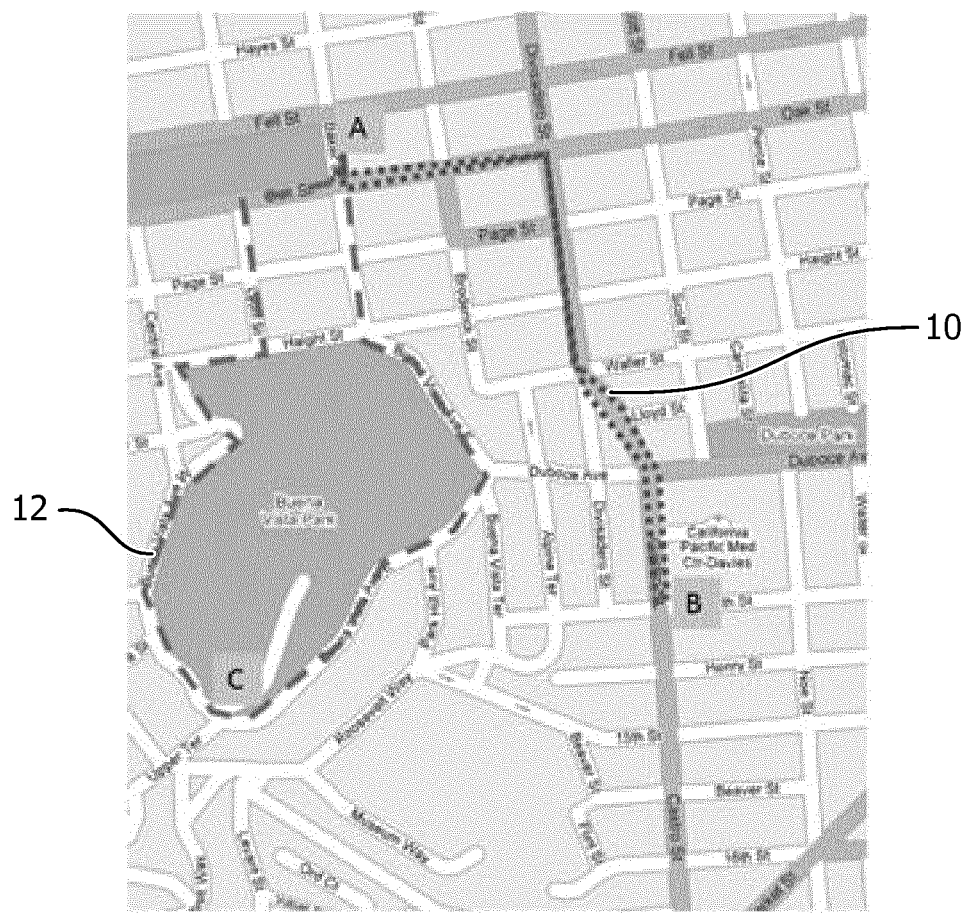
FIG. 2 is a schematic diagram that illustrates an example path classified as utilitarian by a geometric evaluation system and an example path classified as health-related by the geometric evaluation system, the path classifications based on movement sensor data, in accordance with an embodiment of the invention.

Disclosed herein are certain embodiments of a geometric evaluation system, apparatus, and method (herein, also collectively referred to as a geometric evaluation system) that may provide a user with contextual intelligence to assist a user in a given task. Certain embodiments of a geometric evaluation system are related to health self-management and, especially, digital support for a user to become physically more active in daily life. Also, certain embodiments of a geometric evaluation system can be used for automatic assessment of mental and cognitive state of a subject. For instance, in the area of health management, a geometric evaluation system can address a problem of less effective coaching due to unknown purpose of activity by providing a method for identifying whether the activity is utilitarian or health-related, while in the process, reduce computational requirements of existing activity monitoring systems and/or provide an improvement in accuracy of systems or devices that monitor a user's health and/or behavior. One underlying assumption of a geometric evaluation system is that geometry of an ambulatory path of a user can indicate a purpose, or a semantic connotation of the journey. The purpose can be used in a health program to more accurately monitor and motivate a user to increase physical activity, which is an important element in the self-management of many common diseases.

Digressing briefly, most of the personal health programs based on applications track the location of the user and can measure the length of the trajectory, speed of movement, step counts, means of transportation, and other measures related to the path of movement. For instance, data from wearable sensor devices can track the activity of the user, but the sensing of the purpose of a particular activity is very difficult to sense and therefore the activity sensing often lacks a semantic frame of reference. In contrast, certain embodiments of a geometric evaluation system characterize the geometry of an ambulatory trajectory. In other words, the geometry of a path is characterized by a path score based on a ratio of an area the path encloses and a square of a length of the path. The information of the path based on the score can be used in many ways in various connected health services. By using geometric evaluation of the path, contextual intelligence gathering may utilize fewer computational resources and/or improve the accuracy of existing systems, while establishing a purpose for the activity to engendering the efficient and accurate provision of useful information (e.g., contextual messages).

Having summarized certain features of a geometric evaluation system of the present disclosure, reference will now be made in detail to the description of a geometric evaluation system as illustrated in the drawings. While a geometric evaluation system will be described in connection with these drawings, there is no intent to limit geometric evaluation systems to the embodiment or embodiments disclosed herein. For instance, though emphasis is placed below on describing the use of a geometric evaluation system as an alternative to existing systems, some embodiments may use a geometric evaluation system as a supplement to existing systems, such as to improve or confirm accuracy. Further, although the description identifies or describes specifics of one or more embodiments, such specifics are not necessarily part of every embodiment, nor are all various stated advantages necessarily associated with a single embodiment or all embodiments. On the contrary, the intent is to cover all alternatives, modifications and equivalents included within the spirit and scope of the disclosure as defined by the appended claims. Further, it should be appreciated in the context of the present disclosure that the claims are not necessarily limited to the particular embodiments set out in the description.

Attention is directed to FIGS. 1A-1B, which illustrate example paths derived from data points sensed by a location detecting device (e.g., Global Positioning System (GPS) receiver) held by a user that tracks movement of a user engaged in activities during the week and weekend, respectively. In FIG. 1A, movement sensor data in the form, in this example, of GPS location coordinates are plotted over the course of several weeks for weekday travel routes as a user travels from home (location A) to work (location C) and back, to and from a supermarket (B), and to other utilitarian destinations (D). The example pattern in FIG. 1A resembles a star, as reflected by the shared path of ingress and egress relative to home and the other recurring locations (B, C, and D). In contrast, and referring to FIG. 1B, the GPS plots are collected over a span of several weekends for an active cyclist (the location A representing the recurring location from where the cyclist begins his ride, such as a bike path parking lot), and the other points B-D representing various markers along the paths. In this example, the paths are health-related, representing cycling activity across, for instance, a countryside around town, with the pattern more flower-like in appearance. In particular, the paths of FIG. 1B are more amenable to a higher geometric score, as explained further below.

Referring now to FIG. 2, shown is an example path 10 classified as utilitarian (A-B) by a geometric evaluation system and an example path 12 (A-C) classified as health-related by the geometric evaluation system. The paths 10, 12 are represented with dashed lines, the paths 10, 12 based on movement sensor data in the form of location coordinate data (e.g., GPS data points) spanning to and from recurring locations A-B in path 10 and recording travel along a somewhat circular path 12 beginning at A, passing through location C, and returning to A. For instance, a user may have a GPS receiver in his or her phone, or integrated in his or her wearable device, which tracks the movement of the user. In this example, the user travelling along the path 10 may be traveling from home (recurring location A) to a grocery store (or other utilitarian destination), and then returning along the same path. As for the path 12, the user may walk, run, cycle, etc. to a nearby park, travel around the park past marker C, and return home along a different path than from which he or she began the travel. It is noted that, unlike the path 10, the path 12 encloses an area and does not return along the same path. In one embodiment, the geometric evaluation system (whether embodied as a wearable device, portable device (e.g., smartphone), and/or a computing system that receives sensor data from either of the two aforementioned types of devices) tracks and records location data points along the path 10 or 12 traveled by a user. Based on the location data, the geometric evaluation system computes the length of the path L and the enclosed area A. In the case of path 10 where the user returns exactly along the same path from place B (to A), the area A is approximately equal to zero (0). Movement along this path is referred to as utilitarian or a utilitarian trip because the purpose of the trip is evidently to visit place B for some utility (e.g., shop for groceries at a supermarket). In the case of path 12, where the user travels a loop, the area is significantly larger, so the most likely purpose of the trip is the trip itself. That is, the trip is for the purpose of advancing a health benefit associated with physical activity of the user. As explained further below, a score is determined based on the parameters of area (or equivalent of area) and length, classification of the trip is performed, and then feedback is provided. That is, based on the classification of the path as health-related, the geometric evaluation system can provide contextual intelligence to the user in the form of feedback related to the health of the user or progress toward a goal or a cognitive state of the user.

Some example operations implemented by certain embodiments of a geometric evaluation system are explained further below, but generally may include one or more of the following: identifying recurring locations of user (e.g., work, home, sports or recreational area parking lot, etc.), tracking locations by dividing location tracking into segments (e.g., arrivals and departures), determining a type of activity of user (e.g., walking, running, cycling, etc.), computing the path length L and the area A (or area equivalent) enclosed by the path, computing a score for each segment, classifying each segment as being a utilitarian or health-related ambulatory journey, and then providing feedback to the user based on whether a segment is utilitarian or health-related.

Figure 3:
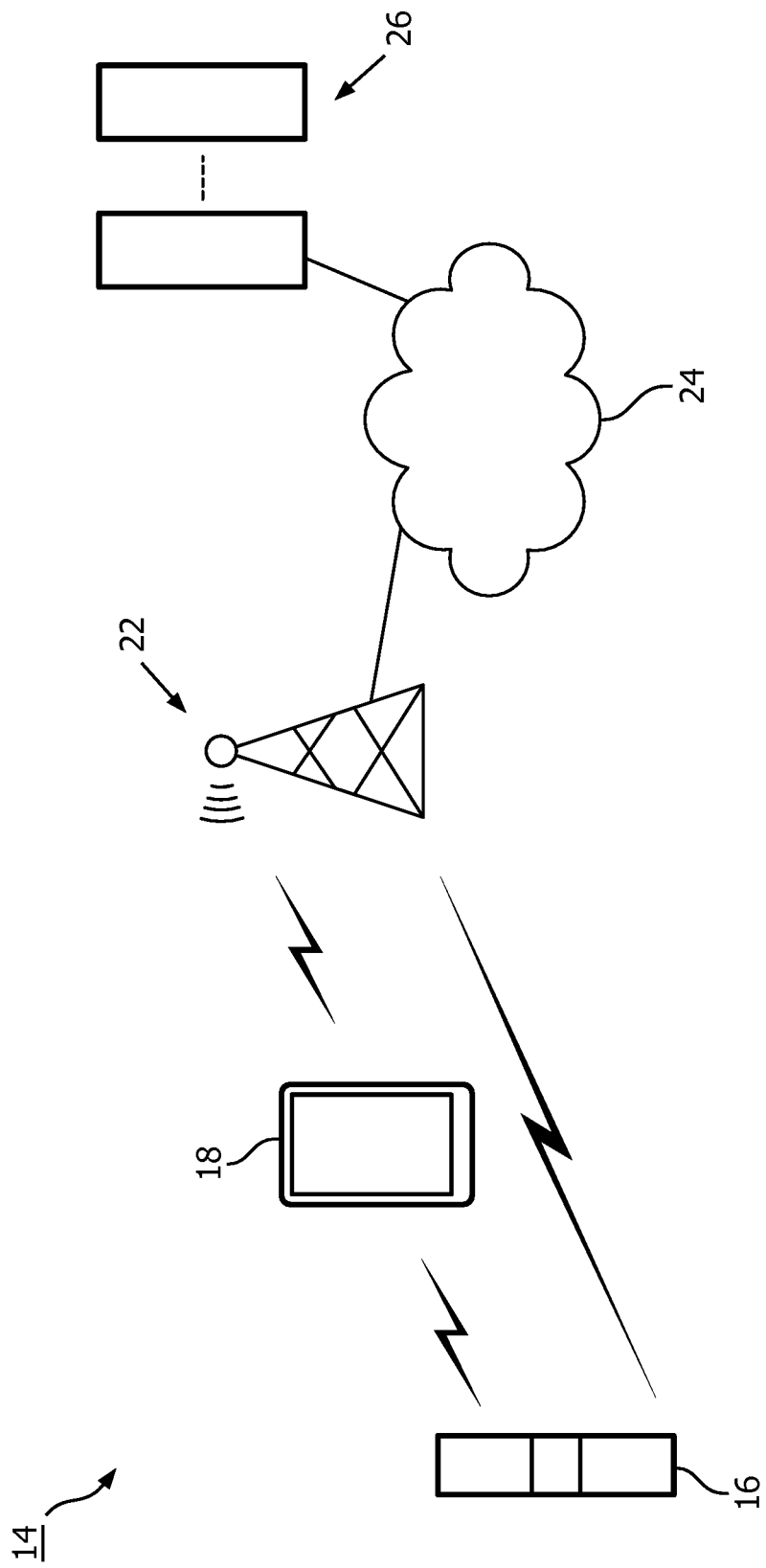
FIG. 3 is a schematic diagram that illustrates an example environment in which a geometric evaluation system is used in accordance with an embodiment of the invention.
Figure 4:
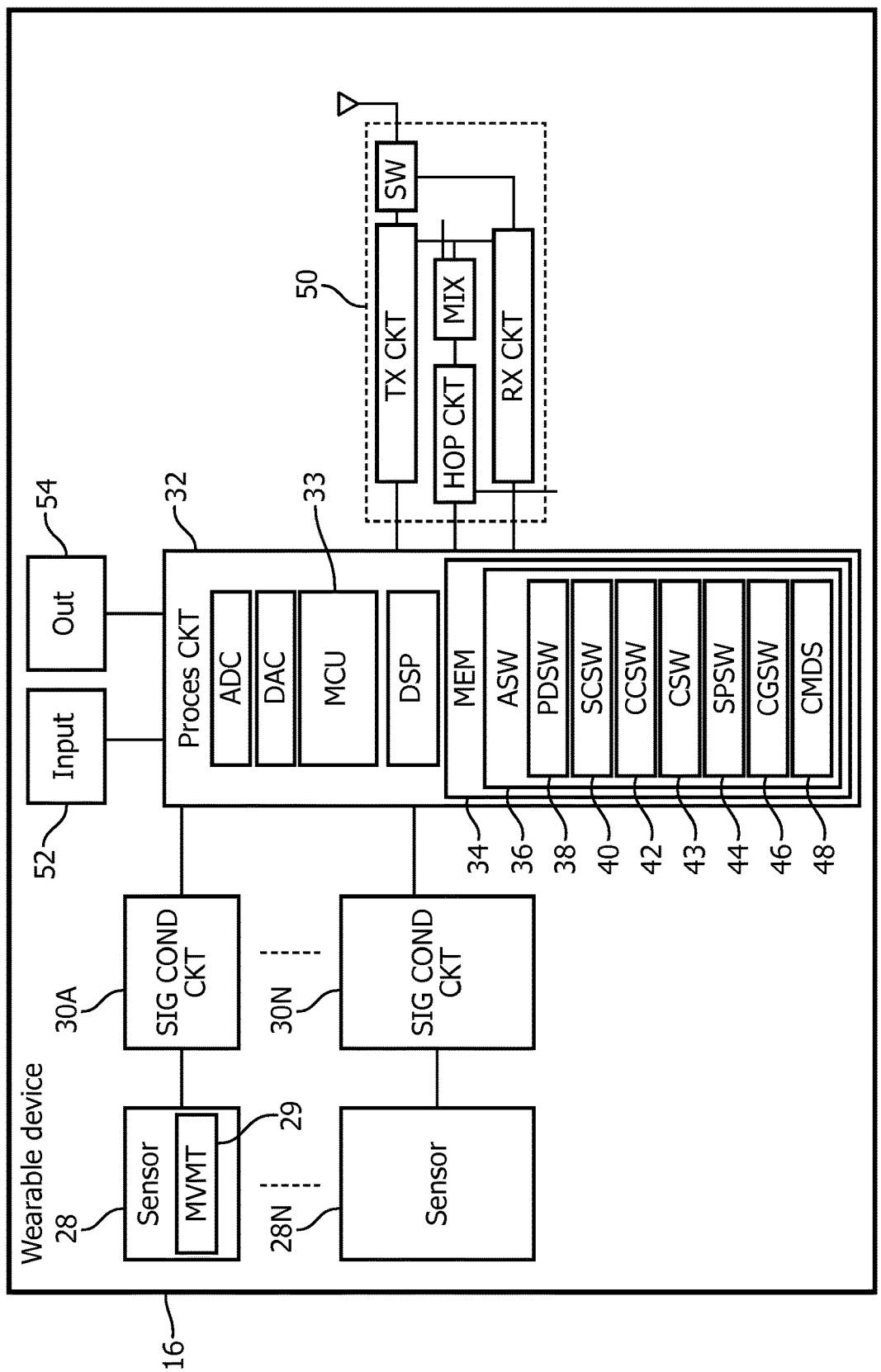
FIG. 4 is a schematic diagram that illustrates an example wearable device in which all or a portion of the functionality of a geometric evaluation system may be implemented, in accordance with an embodiment of the invention.

Having described example operations and example illustrations of a geometric evaluation system, attention is directed to FIG. 3, which illustrates an example environment 14 in which certain embodiments of a geometric evaluation system may be implemented. It should be appreciated by one having ordinary skill in the art in the context of the present disclosure that the environment 14 is one example among many, and that some embodiments of a geometric evaluation system may be used in environments with fewer, greater, and/or different components that those depicted in FIG. 3. The environment 14 comprises a plurality of devices that enable communication of information throughout one or more networks. The depicted environment 14 comprises a wearable device 16, an electronics (portable) device 18, a cellular network 22, a wide area network 24 (e.g., also described herein as the Internet), and a remote computing system 26. The wearable device 16, as described further in association with FIG. 4, is typically worn by the user (e.g., around the wrist or torso or attached to an article of clothing), and comprises a plurality of sensors that track physical activity of the user (e.g., steps, swim strokes, pedaling strokes, etc.), sense/measure or derive physiological parameters (e.g., heart rate, respiration, skin temperature, etc.) based on the sensor data, and optionally sense various other parameters (e.g., outdoor temperature, humidity, location, etc.) pertaining to the surrounding environment of the wearable device 16. For instance, in some embodiments, the wearable device 16 may comprise a global navigation satellite system (GNSS) receiver, including a GPS receiver, which tracks and provides location coordinates for the device. Some embodiments of the wearable device 16 may include a motion or inertial tracking sensor, including an accelerometer and/or a gyroscope. A representation of such gathered data may be communicated to the subject via an integrated display on the wearable device and/or on another device or devices.

Also, such data gathered by the wearable device 16 may be communicated (e.g., continually, periodically, and/or aperiodically) to one or more electronics devices, such as the electronics device 18. Such communication may be achieved wirelessly (e.g., using near field communications (NFC) functionality, Blue-tooth functionality, etc.) and/or according to a wired medium (e.g., universal serial bus (USB), etc.). Further discussion of the wearable device 16 is described below in association with FIG. 4.

The electronic device 18 may be embodied as a smartphone, mobile phone, cellular phone, pager, stand-alone image capture device (e.g., camera), among other handheld and portable computing/communication devices with communication (e.g., wireless communication, including telephony functionality) and optionally built-in, image capture/recording functionality. In the depicted embodiment of FIG. 3, the electronic device 18 is a smartphone. Further discussion of the electronic device 18 is described below in association with FIG. 5.

The cellular network 22 may include the necessary infrastructure to enable cellular communications by the electronic device 18 and optionally the wearable device 16. There are a number of different digital cellular technologies suitable for use in the cellular network 22, including: GSM, GPRS, CDMAOne, CDMA2000, Evolution-Data Optimized (EV-DO), EDGE, Universal Mobile Telecommunications System (UMTS), Digital Enhanced Cordless Telecommunications (DECT), Digital AMPS (IS-136/TDMA), and Integrated Digital Enhanced Network (iDEN), among others.

The wide area network 24 may comprise one or a plurality of networks that in whole or in part comprise the Internet. The electronics device 18 and optionally wearable device 16 access one or more of the devices of the computing system 26 via the Internet 24, which may be further enabled through access to one or more networks including PSTN (Public Switched Telephone Networks), POTS, Integrated Services Digital Network (ISDN), Ethernet, Fiber, DSL/ADSL, among others.

The computing system 26 comprises one or more devices coupled to the wide area network 24, including one or more computing devices networked together, including an application server(s) and data storage. The computing system 26 may serve as a cloud computing environment (or other server network) for the electronics device 18 and/or wearable device 16, performing processing and data storage on behalf of (or in some embodiments, in addition to) the electronics devices 18 and/or wearable device 16. In some embodiments, one or more of the functionality of the computing system 26 may be performed at the respective devices 16 and/or 18. Further discussion of the computing system 26 is described below in association with FIG. 6.

An embodiment of a geometric evaluation system may comprise the wearable device 16, the electronic device 18, and/or the computing system 26. In other words, one or more of the aforementioned devices 16, 18, and 26 may implement the functionality of the geometric evaluation system. For instance, the wearable device 16 may comprise all of the functionality of a geometric evaluation system, enabling the user to avoid the need for Internet connectivity and/or carrying a smartphone 18 around. In some embodiments, the functionality of the geometric evaluation system may be implemented using a combination of the wearable device 16 and the electronics device 18 and/or the computing system 26 (with or without the electronic device 18). For instance, the wearable device 16 may present contextual messages via a user interface and provide sensing functionality, yet rely on a remote data structure of contextual messages and remote processing. In other words, access to a data structure of contextual messages, the processing/determinations of plural parameters including the area (or area equivalent), length, and the computation of scores and determination of classifications may be implemented at a device other than the wearable device 16, including one or a combination of the electronics device 18 or the computing system 26. As an example, the wearable device 16 may communicate sensed data (e.g., location coordinates, motion data, etc.) to one of the devices external to the wearable device 16, where all other processing is performed, and then the contextual message to be presented by the wearable device 16 is received from one of the external devices by the wearable device 16 and presented. One benefit to the latter embodiment is that off-loading of the computational resources of the wearable device 16 is enabled, conserving power consumed by the wearable device 16. In some embodiments, the electronic device 18 may perform all of the functionality of the geometric evaluation system, or in some embodiments, cooperate with the computing system 26 (e.g., provide the location sensing functionality, and rely on the computing system 26 for contextual message access and storage and processing). Again, the power consumption may be off-loaded from battery-based devices, where the generally larger battery of a smartphone 18 is better suited to handle power requirements for the geometric evaluation system than the wearable, and where a computing system 26 is even better suited than the smartphone 18 to handle the power requirements for the geometric evaluation system. Also, the compute resources generally increase from the wearable device 16, to the electronics device 18, and then the computing system 26, enabling improvements in processing speed as off-loading occurs from the wearable device 16 to the electronics device 18, and from the electronics device 18 to the computing system 26.

Attention is now directed to FIG. 4, which illustrates an example wearable device 16 in which all or a portion of the functionality of a geometric evaluation system may be implemented. That is, FIG. 4 illustrates example circuitry for the example wearable device 16, and in particular, underlying circuitry and software (e.g., architecture) of the wearable device 16. It should be appreciated by one having ordinary skill in the art in the context of the present disclosure that the architecture of the wearable device 16 depicted in FIG. 4 is but one example, and that in some embodiments, additional, fewer, and/or different components may be used to achieve similar and/or additional functionality. In one embodiment, the wearable device 16 comprises a plurality of sensors 28 (e.g., 28A-28N), which collectively include one or more movement detecting sensors (MVMT) 29, one or more signal conditioning circuits 30 (e.g., SIG COND CKT 30A—SIG COND CKT 30N) coupled respectively to the sensors 28, and a processing circuit 32 (PROCES CKT) that receives the conditioned signals from the signal conditioning circuits 30. In one embodiment, the processing circuit 32 comprises an analog-to-digital converter (ADC), a digital-to-analog converter (DAC), a microcontroller (e.g., MCU) 33, a digital signal processor (DSP), and memory (MEM) 34. Note that the microcontroller 33 and digital signal processor are also referred to herein individually as a processor. In some embodiments, the processing circuit 32 may comprise fewer or additional components than those depicted in FIG. 4. For instance, in one embodiment, the processing circuit 32 may consist of the microcontroller 33. The memory 34 comprises an operating system (OS) and application software (ASW) 36. The application software comprises executable code/instructions comprising a plurality of software modules (e.g., executable code) including parameter determination software (PDSW) 38, score computation software (SCSW) 40, correlation coefficient software (CCSW) 42, classification software (CSW) 43, supplemental path software (SPSW) 44, cognitive software (CGSW) 46, and a contextual message data structure (CMDS) 48 with plural entries for respective contextual messages. In some embodiments, the contextual message data structure 48 may be in memory 34 or other storage and a separate module from the application software 36. The application software 36 also comprises executable code to process the signals (and associated data) measured by the sensors and record and/or derive physiological parameters, such as heart rate, blood pressure, respiration, perspiration, etc. The application software 36 also comprises communications software, such as that used to enable the wearable device 16 to operate according to one or more of a plurality of different communication technologies (e.g., NFC, Bluetooth, Wi-Fi, including 802.11, GSM, LTE, CDMA, WCDMA, Zigbee, etc.). The communications software may also include browser software in some embodiments to enable Internet connectivity. The communications software may also be used to access certain services, such as mapping/place location services. These services may be used in some embodiments of a geometric evaluation system, and in some instances, may not be used. In some embodiments, the communications software may be in separate or other memory 34, or part of additional application software that is separate from the application software 36.

In one embodiment, the processing circuit 32 is coupled to a communications circuit 50. The communications circuit 50 serves to enable wireless communications between the wearable device 16 and other devices, including the electronics device 18 and the computing system 26, among other devices. The communications circuit 50 is depicted as a Bluetooth circuit, though not limited to this transceiver configuration. For instance, in some embodiments, the communications circuit 50 may be embodied as any one or a combination of an NFC circuit, Wi-Fi circuit, transceiver circuitry based on Zigbee, 802.11, GSM, LTE, CDMA, WCDMA, among others such as optical or ultrasonic based technologies. The processing circuit 32 is further coupled to input/output (I/O) devices or peripherals, including an input interface 52 (INPUT) and output interface 54 (OUT). Note that in some embodiments, functionality for one or more of the aforementioned circuits and/or software may be combined into fewer components/modules, or in some embodiments, further distributed among additional components/modules. For instance, the processing circuit 32 may be packaged as an integrated circuit that includes the microcontroller 33, the DSP, and memory 34, whereas the ADC and DAC may be packaged as a separate integrated circuit coupled to the processing circuit 32. In some embodiments, one or more of the functionality for the above-listed components may be combined, such as functionality of the DSP performed by the microcontroller 33.

The sensors 28 are selected to perform detection and measurement of a plurality of physiological and behavioral parameters, including heart rate, heart rate variability, heart rate recovery, blood flow rate, activity level, muscle activity (e.g., movement of limbs, repetitive movement, core movement, body orientation/position, power, speed, acceleration, etc.), muscle tension, blood volume, blood pressure, blood oxygen saturation, respiratory rate, perspiration, skin temperature, body weight, and body composition (e.g., body mass index or BMI). At least one of the sensors 28 may be embodied as movement detecting sensors 29, including inertial sensors (e.g., gyroscopes, single or multi-axis accelerometers, such as those using piezoelectric, piezoresistive or capacitive technology in a microelectromechanical system (MEMS) infrastructure for sensing movement) and/or as GNSS sensors, including a GPS receiver to facilitate determinations of distance, speed, acceleration, location, altitude, etc. (e.g., location data, or generally, sensing movement), in addition to or in lieu of the accelerometer/gyroscope. The sensors 28 may also include flex and/or force sensors (e.g., using variable resistance), electromyographic sensors, electrocardiographic sensors (e.g., EKG, ECG) magnetic sensors, photoplethysmographic (PPG) sensors, bio-impedance sensors, infrared proximity sensors, acoustic/ultrasonic/audio sensors, a strain gauge, galvanic skin/sweat sensors, pH sensors, temperature sensors, pressure sensors, and photocells. The sensors 28 may include other and/or additional types of sensors for the detection of, for instance, barometric pressure, humidity, outdoor temperature, etc. In some embodiments, GNSS functionality may be achieved via the communications circuit 50 or other circuits coupled to the processing circuit 32.

The signal conditioning circuits 30 include amplifiers and filters, among other signal conditioning components, to condition the sensed signals including data corresponding to the sensed physiological parameters and/or location signals before further processing is implemented at the processing circuit 32. Though depicted in FIG. 4 as respectively associated with each sensor 28, in some embodiments, fewer signal conditioning circuits 30 may be used (e.g., shared for more than one sensor 28). In some embodiments, the signal conditioning circuits 30 (or functionality thereof) may be incorporated elsewhere, such as in the circuitry of the respective sensors 28 or in the processing circuit 32 (or in components residing therein). Further, although described above as involving unidirectional signal flow (e.g., from the sensor 28 to the signal conditioning circuit 30), in some embodiments, signal flow may be bi-directional. For instance, in the case of optical measurements, the microcontroller 33 may cause an optical signal to be emitted from a light source (e.g., light emitting diode(s) or LED(s)) in or coupled to the circuitry of the sensor 28, with the sensor 28 (e.g., photocell) receiving the reflected/refracted signals.

The communications circuit 50 is managed and controlled by the processing circuit 32. The communications circuit 50 is used to wirelessly interface with the electronics device 18 (FIG. 3) and/or one or more devices of the computing system 26. In one embodiment, the communications circuit 50 may be configured as a Bluetooth transceiver, though in some embodiments, other and/or additional technologies may be used, such as Wi-Fi, GSM, LTE, CDMA and its derivatives, Zigbee, NFC, among others. In the embodiment depicted in FIG. 4, the communications circuit 50 comprises a transmitter circuit (TX CKT), a switch (SW), an antenna, a receiver circuit (RX CKT), a mixing circuit (MIX), and a frequency hopping controller (HOP CTL). The transmitter circuit and the receiver circuit comprise components suitable for providing respective transmission and reception of an RF signal, including a modulator/demodulator, filters, and amplifiers. In some embodiments, demodulation/modulation and/or filtering may be performed in part or in whole by the DSP. The switch switches between receiving and transmitting modes. The mixing circuit may be embodied as a frequency synthesizer and frequency mixers, as controlled by the processing circuit 32. The frequency hopping controller controls the hopping frequency of a transmitted signal based on feedback from a modulator of the transmitter circuit. In some embodiments, functionality for the frequency hopping controller may be implemented by the microcontroller 33 or DSP. Control for the communications circuit 50 may be implemented by the microcontroller 33, the DSP, or a combination of both. In some embodiments, the communications circuit 50 may have its own dedicated controller that is supervised and/or managed by the microcontroller 33.

In operation, a signal (e.g., at 2.4 GHz) may be received at the antenna and directed by the switch to the receiver circuit. The receiver circuit, in cooperation with the mixing circuit, converts the received signal into an intermediate frequency (IF) signal under frequency hopping control attributed by the frequency hopping controller and then to baseband for further processing by the ADC. On the transmitting side, the baseband signal (e.g., from the DAC of the processing circuit 32) is converted to an IF signal and then RF by the transmitter circuit operating in cooperation with the mixing circuit, with the RF signal passed through the switch and emitted from the antenna under frequency hopping control provided by the frequency hopping controller. The modulator and demodulator of the transmitter and receiver circuits may be frequency shift keying (FSK) type modulation/demodulation, though not limited to this type of modulation/demodulation, which enables the conversion between IF and baseband. In some embodiments, demodulation/modulation and/or filtering may be performed in part or in whole by the DSP. The memory 34 stores firmware that is executed by the microcontroller 33 to control the Bluetooth transmission/reception.

Though the communications circuit 50 is depicted as an IF-type transceiver, in some embodiments, a direct conversion architecture may be implemented. As noted above, the communications circuit 50 may be embodied according to other and/or additional transceiver technologies.

The processing circuit 32 is depicted in FIG. 4 as including the ADC and DAC. For sensing functionality, the ADC converts the conditioned signal from the signal conditioning circuit 30 and digitizes the signal for further processing by the microcontroller 33 and/or DSP. The ADC may also be used to convert analogs inputs that are received via the input interface 52 to a digital format for further processing by the microcontroller 33. The ADC may also be used in baseband processing of signals received via the communications circuit 50. The DAC converts digital information to analog information. Its role for sensing functionality may be to control the emission of signals, such as optical signals or acoustic signal, from the sensors 28. The DAC may further be used to cause the output of analog signals from the output interface 54. Also, the DAC may be used to convert the digital information and/or instructions from the microcontroller 33 and/or DSP to analog signal that are fed to the transmitter circuit. In some embodiments, additional conversion circuits may be used.

The microcontroller 33 and the DSP provide the processing functionality for the wearable device 16. In some embodiments, functionality of both processors may be combined into a single processor, or further distributed among additional processors. The DSP provides for specialized digital signal processing, and enables an offloading of processing load from the microcontroller 33. The DSP may be embodied in specialized integrated circuit(s) or as field programmable gate arrays (FPGAs). In one embodiment, the DSP comprises a pipelined architecture, with comprises a central processing unit (CPU), plural circular buffers and separate program and data memories according to a Harvard architecture. The DSP further comprises dual busses, enabling concurrent instruction and data fetches. The DSP may also comprise an instruction cache and I/O controller, such as those found in Analog Devices SHARC® DSPs, though other manufacturers of DSPs may be used (e.g., Freescale multi-core MSC81xx family, Texas Instruments C6000 series, etc.). The DSP is generally utilized for math manipulations using registers and math components that may include a multiplier, arithmetic logic unit (ALU, which performs addition, subtraction, absolute value, logical operations, conversion between fixed and floating point units, etc.), and a barrel shifter. The ability of the DSP to implement fast multiply-accumulates (MACs) enables efficient execution of Fast Fourier Transforms (FFTs) and Finite Impulse Response (FIR) filtering. Some or all of the DSP functions may be performed by the microcontroller 33. The DSP generally serves an encoding and decoding function in the wearable device 16. For instance, encoding functionality may involve encoding commands or data corresponding to transfer of information to the electronics device 18 or a device of the computing system 26. Also, decoding functionality may involve decoding the information received from the sensors 28 (e.g., after processing by the ADC).

The microcontroller 33 comprises a hardware device for executing software/firmware, particularly that stored in memory 34. The microcontroller 33 can be any custom made or commercially available processor, a central processing unit (CPU), a semiconductor based microprocessor (in the form of a microchip or chip set), a macroprocessor, or generally any device for executing software instructions. Examples of suitable commercially available microprocessors include Intel's® Itanium® and Atom® microprocessors, to name a few non-limiting examples. The microcontroller 33 provides for management and control of the wearable device 16, including determining physiological parameters or location coordinates based on the sensors 28, and for enabling communication with the electronics device 18 and/or a device of the computing system 26, and for the computations/determinations for the geometric evaluation system.

The memory 34 can include any one or combination of volatile memory elements (e.g., random access memory (RAM, such as DRAM, SRAM, SDRAM, etc.)) and non-volatile memory elements (e.g., ROM, Flash, solid state, EPROM, EEPROM, etc.). Moreover, the memory 34 may incorporate electronic, magnetic, and/or other types of storage media.

The software in memory 34 may include one or more separate programs, each of which comprises an ordered listing of executable instructions for implementing logical functions. In the example of FIG. 4, the software in the memory 34 includes a suitable operating system and the application software 36 that includes a plurality of software modules 38-48 for implementing certain embodiments of a geometric evaluation system and algorithms for determining physiological and/or behavioral measures and/or other information (e.g., including location, speed of travel, etc.) based on the output from the sensors 28. The raw data from the sensors 28 may be used by the algorithms to determine various physiological and/or behavioral measures (e.g., heart rate, biomechanics, such as swinging of the arms), and may also be used to derive other parameters, such as energy expenditure, heart rate recovery, aerobic capacity (e.g., VO2 max, etc.), among other derived measures of physical performance In some embodiments, these derived parameters may be computed externally (e.g., at the electronics devices 18 or one or more devices of the computing system 26) in lieu of, or in addition to, the computations performed local to the wearable device 16. The application software may also include communications software to enable communications with other electronics devices. The operating system essentially controls the execution of other computer programs, such as the application software and communications software, and provides scheduling, input-output control, file and data management, memory management, and communication control and related services. The memory 34 may also include one or more data structures, including the contextual message data structure 48 and other data structures that include user data, including weight, height, age, gender, goals, body mass index (BMI) that are used by the microcontroller 33 executing the executable code of the algorithms to accurately interpret the measured physiological and/or behavioral data. The contextual message data structure 48 also comprises historical data relating past recorded data to prior paths, which enables the application software 36 to make comparisons of paths to enable access to the appropriate contextual messages (e.g., including repeating healthy behavior). Note that the contextual message data structure may comprise plural data structures, including linked lists, relational data bases, among others. In some embodiments, the contextual message data structure 48 and/or other data structures (e.g., of user data) may be stored elsewhere, such as at the electronics device 18 and/or at one or more devices of the computing system 26 in lieu of, or in addition to being stored at the wearable device 16.

Explaining the application software 36 further, and assuming an embodiment where functionality of the geometric evaluation system is implemented entirely on the wearable device 16, the GPS functionality of the sensors 28 collects location data (e.g., location coordinates). The application software 36 collects location data by sampling the location readings from the sensor 28 over a period of time (e.g., hours, days, weeks, etc.). The application software 36 discovers recurring locations where the user remains for a long time. Typical recurring locations include the home and a work place of the user. These tracked locations (e.g., over a period of time, such as trips taken during a week) are divided into segments by the application software 36, the location track divided into segments by the arrivals and departures from the recurring places. A segment is generally understood herein as the path for which travel by the user is monitored. For instance, path 10 (FIG. 2) is a segment, and path 12 (FIG. 2) is a segment. As another example, a path configured as a figure-eight may be treated by the software as a single segment, as would a chain of loops. In some embodiments, the aforementioned paths may be further broken down into smaller segments. The application software 36 may also collect information about the means of ambulation. For instance, the GPS data (which may include time coordinates) may be used by the application software 36 to determine speed of travel, which may indicate whether the user is moving within a vehicle, on a bicycle, or walking or running. In some embodiments, other and/or additional data may be used to assess the type of activity, including physiological data (e.g., heart rate, respiration rate, galvanic skin response, etc.). The application software 36 selects segments which mainly contain physical activity of the user (e.g., walking, running, cycling). For instance, the application software 36 excludes segments or portions of segments (or excludes the recording of location data for segments) where the user is traveling by car. It is generally understood that many geo-tracking libraries provide detection of the means for transportation. In each segment, the parameter determination software 38 computes the path length L and the area (A) enclosed by the path. The computation of these values based on a track of location points can be performed using well-known techniques. For each segment (e.g., path 12 from A, past C, and back to A), the score computation software 40 computes a score which characterizes the described geometrical property. For instance, paths that do not enclose an area (e.g., same path between destinations is that taken by the user) generally produce a low score (e.g., closer to zero). The details of the score computation are discussed further below. Depending on the score, each segment is classified by the classification software 43 as being a utilitarian or health-related ambulatory journey.

Based on the classification, the application software 36 accesses a corresponding entry in the contextual message data structure 48 to provide a contextual message that conveys feedback, summaries, advice, and/or insights related to utilitarian and health-related trips. Related to the appropriate access of contextual messages is a feature whereby the supplemental path software 44 may recommend changing a recurring health-related or utilitarian trip to a round-trip loop (e.g., using an alternative path based on GPS data) which for a pair of given endpoints will in most cases lead to a longer total path. For instance, paths that result in a low score and/or data indicating a user's deficiency as to health-related parameters (e.g., deficiency in meeting health-related goals) may flag and/or trigger the activation of the supplemental path software 44, which by determining a supplemental path, advances a coaching goal of increasing user activity (e.g., to improve health). In one embodiment, the application software 36 may propose changing a utilitarian trip to a health-related trip. One method used by the application software 36 (e.g., the supplemental path software 44) is to convert a path, such as path 10, into a path that more resembles path 12 (FIG. 2) or paths shown in FIG. 1B (e.g., more flower-like). In other words, the supplemental path may be one that generates a larger score (e.g., covers or surrounds more area and/or has a longer length). For instance, the application software 36 may detect over a period of time that the user walks frequently (e.g., several times a week, taking say, a twenty (20) minute walk) along a short path to a nearby shop and returns along the same path. Since the score is lower (e.g., zero or approximately zero), the supplemental path software 44 determines an alternative path with a larger score (e.g., longer path length and/or larger area), such as to make the trip health-related, and accesses a contextual message that suggests to, and/or encourages, the user to take the more health-conscious path (e.g., resulting in healthier behavior) and also providing feedback related to the trip. The contextual message may comprise a subjective and/or objective measure, such as "by changing the path, you will reach the 30 minute daily activity recommendation."

In one embodiment, similar to the description above, a contextual message resulting from implementation of the supplemental path software 44 may be accessed and presented, based on a health-related classification, that encourages a user to consider a supplemental path that further increases the activity when the application software 36 determines, for instance, that the user is deficient in meeting his or her activity goal. In some embodiments, the application software 36 may not implement a supplemental path determination (e.g., supplemental path software may be omitted or inactive), but rather, merely access a contextual message from the contextual message data structure 48 (based on the classification and/or score) that encourages the user to consider a user-formulated path option that increases activity (e.g., to meet or advance a health-related goal). Stated generally, the application software 36 selects contextual messages that provide information that encourage or suggest to the user behavioral changes (e.g., which corresponds to increasing the score, such as by causing an increase in length and/or area of the supplemental path) to improve the user's health. Note that use of the term "supplemental" connotes that the user adds a path to a usual, recorded path, but may also be used to connote a path that is different from the recorded path (except for the recurring location(s)) in an effort to increase user activity.

In some embodiments, the application software 36 uses the recorded data to encourage continued healthy behavior. The application software 36 may determine based on the recorded data (and contextual similarity, based on a comparison of the contextual data surrounding the current path with prior path contextual data stored in the contextual message data structure 48 or elsewhere) that a path or paths taken by the user repeatedly (e.g., multiple times over days and weeks) represent the same or recurring healthy activity/behavior, and recommends to the user to continue to engage in such behavior. The resulting contextual messages may be in the form of coaching, for instance, "Well done! You circled the park path again and it took less time than the previous time." The application software 36 may relate such repeated behavior to health goals or generally health-related targets (e.g., user goals/targets and/or institutional goals/targets, goals and targets used interchangeably herein) and convey the same to the user (e.g., "If you walk this path 4 times per week, you will meet the WHO physical activity target" or "You will reach your personal goal of 50,000 steps in two more trips along the same path"). The application software 36 may also inform the user (via contextual messages) of the physiological benefits (cardio-vascular fitness, muscle strength, etc.) to continued performance of the behavior.

For instance, the application software 36 maintains a list of recurring paths and routines of each user in the contextual message data structure 48 and/or in other data structures in memory 34, or in some embodiments, stored in other storage devices. There may be all kinds of commuting patterns and/or health-related patterns like walking or cycling trips. Typically those health-related patterns/routines are detected, for example, based on duration (e.g., >20 minutes of continuous walking/cycling). In one embodiment, the routines are clustered based on the context (e.g., walk in the evening, cycling trip in the weekend, etc.), where the context is derived by the application software 36 from a pre-defined list (e.g., morning, afternoon, evening, weekday, weekend etc.). The context can be also a location (e.g., park, township, etc.) in embodiments where such data is accessible based on location. The application software 36 compares the stored recurring routines. If a particular recurring routine seems beneficial for the activity goals and has the desired geometric property (e.g., is health-related), the application software 36 may propose: "Your <routine> is good for your activity targets, can you do it more often?". The wording in <routine> is filled based on the context information (e.g., "weekday afternoon"). If the user agrees to do it more often, the application software 36 starts tracking and motivating the user to continue the habit/behavior.

In one embodiment, the score computation software 40 (as executed by the MCU 33, for instance) computes the score from the length of the path L and the area A using the following formula:

$$S = 4\pi \frac{A}{L^2} \quad (1)$$

The maximum value of the score is obtained when the path is a full circle. For instance, a full circle results in a value of S=1. In this case the score for any circle of radius r will obviously converge to:

$$S = 4\pi \frac{\pi r^2}{(2\pi r)^2} = 1 \quad (2)$$

Note that the score is not limited to circular path geometries. For instance, if the path is a square, S=π/4=0.78. In a fully utilitarian trip (e.g., path 10 of FIG. 2: A-B-A), the score is S=0. In one embodiment, a predetermined value (e.g., threshold) is programmed into the classification software 43 that sets the threshold for a utilitarian trip to a low value (e.g., S<0.01), or to one of a plurality of predetermined values that is modified (e.g., via user configuration or automatically) by the path length. In some embodiments, the value is fixed. In some embodiments, the score computation software 40 may account for other contextual attributes, including the means of ambulation.

Note that the score computation software 40 uses location data from GPS functionality of the sensors 28. In some embodiments (e.g., where GPS data is unavailable or inaccurate, or to supplement the GPS-based computations), an estimate of the similarity of a path to one way, and back, may be determined using other measurements. Stated otherwise, the score computation need not be limited to Euclidean geometry. For example, the correlation coefficient software 42 may use a normalized correlation coefficient P of accelerometer data, temperature, air pressure, and/or other data recorded by the wearable device 16 as the user travels on the way from A to B, where the corresponding time-reversed track in going from B to A can be computed to characterize the similarity of the path. In this case, the segments may be scored by the score computation software 40 using a modified version of (1) where the unknown area A is replaced by an equivalent, including PL (where the length is associated with a duration of the sensed activity).

In some embodiments, the cognitive software 46 may use the score to detect the mental and cognitive state of the user and changes thereof. For example, a higher score (e.g., where the user travels in many loop-like patterns) may be an indication of tendency of getting lost easily and confusion. Also a reduction in the score (e.g., closer to zero) may indicate an increased stress or depression of the user. In other words, the score may be used by the cognitive software 46 to detect changes in behavior, such as related to stress. For instance, if the user is under high pressure due to work and is always tired, he or she may not be able to take walks, cycling trips, other activities that create more loop-like path patterns but rather, takes the shortest paths during the day.

Although the application software 36 (and component parts 38-48) are described above as implemented in the wearable device 16, some embodiments may distribute the corresponding functionality among the wearable device 16 and other devices (e.g., electronic device 18 and/or one or more devices of the computing system 26), or in some embodiments, the application software 36 (and component parts 38-40) may be implemented in another device (e.g., the electronics device 18).

The software in memory 34 comprises a source program, executable program (object code), script, or any other entity comprising a set of instructions to be performed. When a source program, then the program may be translated via a compiler, assembler, interpreter, or the like, so as to operate properly in connection with the operating system. Furthermore, the software can be written as (a) an object oriented programming language, which has classes of data and methods, or (b) a procedure programming language, which has routines, subroutines, and/or functions, for example but not limited to, C, C++, Python, Java, among others. The software may be embodied in a computer program product, which may be a non-transitory computer readable medium or other medium.

The input interface 52 comprises an interface (e.g., including a user interface) for entry of user input, such as a button or microphone or sensor (e.g., to detect user input) or touch-type display. The input interface 52 may serve as a communications port for downloaded information to the wearable device 16 (such as via a wired connection). The output interfaces 54 comprises an interface for the presentation or transfer of data, including a user interface (e.g., display screen presenting a graphical user interface) or communications interface for the transfer (e.g., wired) of information stored in the memory, or to enable one or more feedback devices, such as lighting devices (e.g., LEDs), audio devices (e.g., tone generator and speaker), and/or tactile feedback devices (e.g., vibratory motor). In some embodiments, at least some of the functionality of the input and output interfaces 52 and 54 may be combined, including being embodied at least in part as a touch-type display screen for the entry of input and presentation of contextual messages, among other data.

Figure 5:
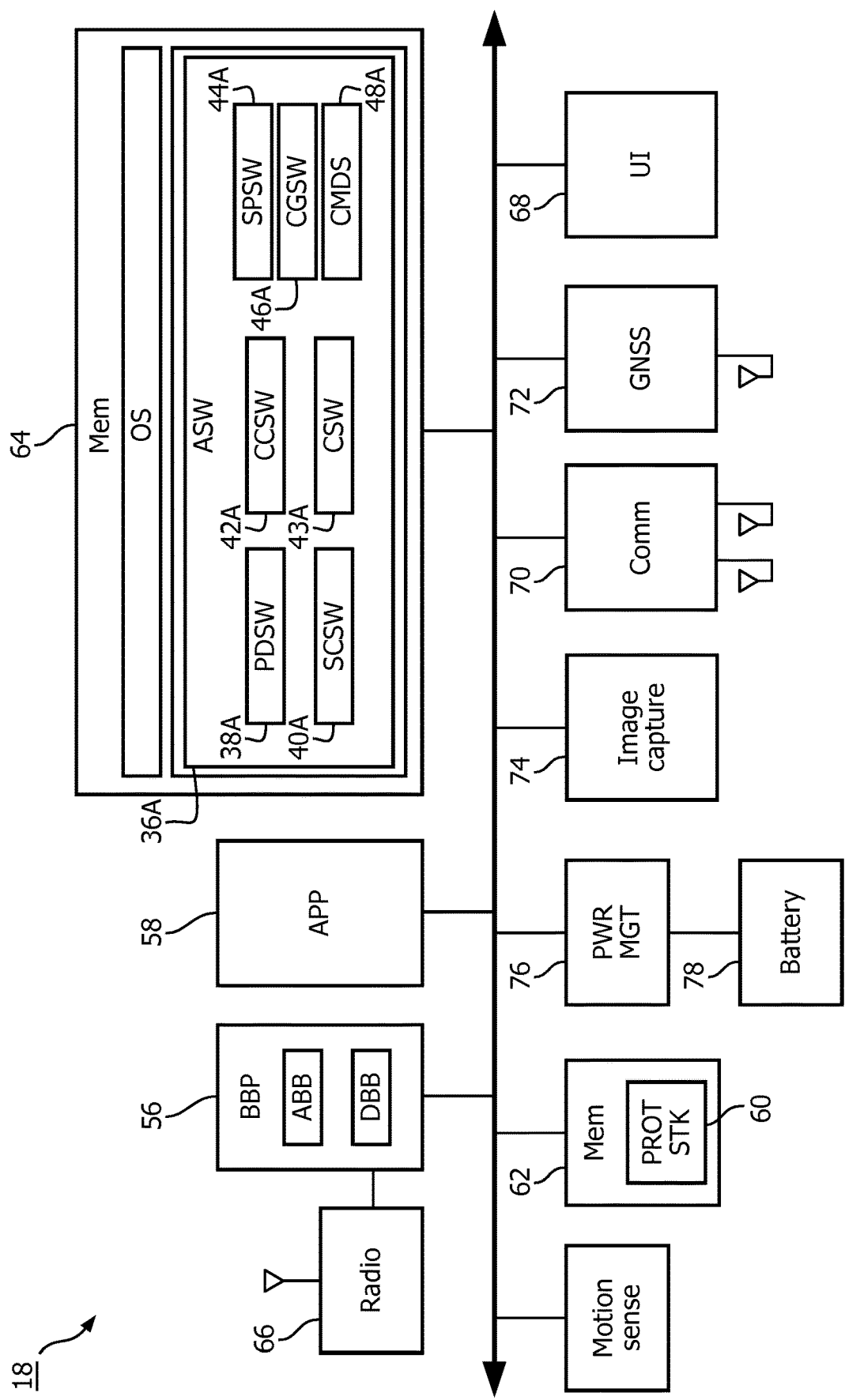
FIG. 5 is a schematic diagram that illustrates an example electronic device in which all or a portion of the functionality of a geometric evaluation system may be implemented, in accordance with an embodiment of the invention.

Referring now to FIG. 5, shown is an example electronic device 18 in which all or a portion of the functionality of a geometric evaluation system may be implemented. In the depicted example, the electronic device 18 is embodied as a smartphone (hereinafter, referred to smartphone 18). It should be appreciated by one having ordinary skill in the art that the logical block diagram depicted in FIG. 5 and described below is one example, and that other designs may be used in some embodiments that incorporate all or a portion of the application software 36A (and its component parts 38A-48A). Note that the application software 36A (and component parts 38A-48A) comprise the functionality of the application software 36 (and component parts 38-48) described above for the wearable device 16, and may include additional software pertinent to smartphone operations (e.g., possibly not found in wearable devices 16). The smartphone 18 comprises at least two different processors, including a baseband processor (BBP) 56 and an application processor (APP) 58. As is known, the baseband processor 56 primarily handles baseband communication related tasks and the application processor 58 generally handles inputs and outputs and all applications other than those directly related to baseband processing. The baseband processor 56 comprises a dedicated processor for deploying functionality associated with a protocol stack (PROT STK) 60, such as a GSM (Global System for Mobile communications) protocol stack, among other functions. The application processor 58 comprises a multi-core processor for running applications, including all or a portion of the application software 36A and its corresponding parts 38A-48A as described above in association with the wearable device 16 of FIG. 4, described further below. The baseband processor 56 and application processor 58 have respective associated memory (e.g., MEM) 62, 64, including random access memory (RAM), Flash memory, etc., and peripherals, and a running clock.

More particularly, the baseband processor 56 may deploy functionality of the protocol stack 60 to enable the smartphone 18 to access one or a plurality of wireless network technologies, including WCDMA (Wideband Code Division Multiple Access), CDMA (Code Division Multiple Access), EDGE (Enhanced Data Rates for GSM Evolution), GPRS (General Packet Radio Service), Zigbee (e.g., based on IEEE 802.15.4), Bluetooth, Wi-Fi (Wireless Fidelity, such as based on IEEE 802.11), and/or LTE (Long Term Evolution), among variations thereof and/or other telecommunication protocols, standards, and/or specifications. The baseband processor 56 manages radio communications and control functions, including signal modulation, radio frequency shifting, and encoding. The baseband processor 56 comprises, or may be coupled to, a radio (e.g., RF front end) 66 and/or a GSM modem having one or more antennas, and analog and digital baseband circuitry (ABB, DBB, respectively in FIG. 5). The radio 66 comprises a transceiver and a power amplifier to enable the receiving and transmitting of signals of a plurality of different frequencies, enabling access to the cellular network 22. The analog baseband circuitry is coupled to the radio 66 and provides an interface between the analog and digital domains of the GSM modem. The analog baseband circuitry comprises circuitry including an analog-to-digital converter (ADC) and digital-to-analog converter (DAC), as well as control and power management/ distribution components and an audio codec to process analog and/or digital signals received (indirectly via the application processor 58 or directly) from the smartphone user interface 68 (e.g., microphone, earpiece, ring tone, vibrator circuits, etc.). The ADC digitizes any analog signals for processing by the digital baseband circuitry. The digital baseband circuitry deploys the functionality of one or more levels of the GSM protocol stack (e.g., Layer 1, Layer 2, etc.), and comprises a microcontroller (e.g., microcontroller unit or MCU, also referred to herein as a processor) and a digital signal processor (DSP, also referred to herein as a processor) that communicate over a shared memory interface (the memory comprising data and control information and parameters that instruct the actions to be taken on the data processed by the application processor 58). The MCU may be embodied as a RISC (reduced instruction set computer) machine that runs a real-time operating system (RTIOS), with cores having a plurality of peripherals (e.g., circuitry packaged as integrated circuits) such as RTC (real-time clock), SPI (serial peripheral interface), I2C (inter-integrated circuit), UARTs (Universal Asynchronous Receiver/Transmitter), devices based on IrDA (Infrared Data Association), SD/MMC (Secure Digital/Multimedia Cards) card controller, keypad scan controller, and USB devices, GPRS crypto module, TDMA (Time Division Multiple Access), smart card reader interface (e.g., for the one or more SIM (Subscriber Identity Module) cards), timers, and among others. For receive-side functionality, the MCU instructs the DSP to receive, for instance, in-phase/quadrature (I/Q) samples from the analog baseband circuitry and perform detection, demodulation, and decoding with reporting back to the MCU. For transmit-side functionality, the MCU presents transmittable data and auxiliary information to the DSP, which encodes the data and provides to the analog baseband circuitry (e.g., converted to analog signals by the DAC).

The application processor 58 operates under control of an operating system (OS) that enables the implementation of a plurality of user applications, including the application software 36. The application processor 58 may be embodied as a System on a Chip (SOC), and supports a plurality of multimedia related features including web browsing to access one or more computing devices of the computing system 26 (FIG. 3) that are coupled to the Internet, email, multimedia entertainment, games, etc. For instance, the application processor 58 may execute interface software (e.g., middleware, such as a browser with or operable in association with one or more application program interfaces (APIs)) to enable access to a cloud computing framework or other networks to provide remote data access/storage/processing, and through cooperation with an embedded operating system, access to calendars, location services, reminders, etc. For instance, in some embodiments, the geometric evaluation system may operate using cloud computing, where the processing of sensor data (e.g., location data, including data received from the wearable device 16 or from integrated sensors within the smartphone 18) and storage of contextual may be achieved by one or more devices of the computing system 26. The application processor 58 generally comprises a processor core (Advanced RISC Machine or ARM), and further comprises or may be coupled to multimedia modules (for decoding/encoding pictures, video, and/or audio), a graphics processing unit (GPU), communication interfaces (COMM) 70, and device interfaces. The communication interfaces 70 may include wireless interfaces, including a Bluetooth (BT) (and/or Zigbee in some embodiments) module that enables wireless communication with an electronic device, including the wearable device 16, other electronic devices, and a Wi-Fi module for interfacing with a local 802.11 network. The application processor 58 further comprises, or is coupled to, a global navigation satellite systems (GNSS) transceiver or receiver (GNSS) 72 for access to a satellite network to provide location services. The device interfaces coupled to the application processor 58 may include the user interface 68, including a display screen. The display screen, similar to a display screen of the wearable device user interface, may be embodied in one of several available technologies, including LCD or Liquid Crystal Display (or variants thereof, such as Thin Film Transistor (TFT) LCD, In Plane Switching (IPS) LCD)), light-emitting diode (LED)-based technology, such as organic LED (OLED), Active-Matrix OLED (AMOLED), or retina or haptic-based technology. For instance, the display screen may be used to present web pages and/or other documents received from the computing system 26 and/or the display screen may be used to present information (e.g., contextual messages) in graphical user interfaces (GUIs) rendered locally in association with the application software 36A. Other user interfaces 68 include a keypad, microphone, speaker, ear piece connector, I/O interfaces (e.g., USB (Universal Serial Bus)), SD/MMC card, among other peripherals. Also coupled to the application processor 58 is an image capture device (IMAGE CAPTURE) 74. The image capture device 74 comprises an optical sensor (e.g., a charged coupled device (CCD) or a complementary metal-oxide semiconductor (CMOS) optical sensor). The image capture device 74 may be used to detect various physiological parameters of a user, including blood pressure based on remote photoplethysmography (PPG). Also included is a power management device 76 that controls and manages operations of a battery 78. The components described above and/or depicted in FIG. 5 share data over one or more busses, and in the depicted example, via data bus 80. It should be appreciated by one having ordinary skill in the art, in the context of the present disclosure, that variations to the above may be deployed in some embodiments to achieve similar functionality.

In the depicted embodiment, the application processor 58 runs the application software 36A, which in one embodiment, includes executable code/instructions comprising a plurality of software modules (e.g., executable code) including parameter determination software (PDSW) 38A, score computation software (SCSW) 40A, correlation coefficient software (CCSW) 42A, classification software (CSW) 43A, supplemental path software (SPSW) 44A, cognitive software (CGSW) 46A, and a contextual message data structure (CMDS) 48A with plural entries for respective contextual messages. Since the description of the application software 36 and software modules 38-48 has been described above in association with the wearable device 16 (FIG. 4), and since the same functionality is present in software 36A-48A, discussion of the same here is omitted for brevity. It is noteworthy, however, that some or all of the software functionality may be implemented in the smartphone 18. For instance, all of the functionality of the application software 36A may be implemented in the smartphone 18, or functionality of the application software 36A may be divided among plural devices of the environment 14 (FIG. 3) in some embodiments. For instance, the sensor data may be received from the wearable device 16, and the smartphone 18 performs the computations and determinations, accesses the contextual message data structure 48 located within memory 64 of the smartphone 18, and provides (e.g., transmits) to the wearable device 16 the appropriate contextual messages (and/or in some embodiments, presents the messages via user interfaces of both devices 16, 18), thus relieving the wearable device of some of the computational burden. In some embodiments, the smartphone 18 may use the GPS data from the wearable device 16 or from the GNSS receiver 72 (and/or motion sensing device(s), such as an accelerometer and/or gyroscope residing in the smartphone 18), perform the computations and determinations, and access the contextual message data structure 48 from one of the devices of the computing system 26. The feedback may be provided by the UI 68 of the smartphone 18 or communicated to the wearable device 16 for output via the output unit 54 (e.g., user interface, FIG. 4), or for presentation by both devices 16 and 18. These and/or other variations are contemplated to be within the scope of the disclosure. The application software 36A may also comprises executable code to process the signals (and associated data) measured by the sensors (of the wearable device 16 as communicated to the smartphone 18, or based on sensors integrated within the smartphone 18) and record and/or derive physiological parameters, such as heart rate, blood pressure, respiration, perspiration, etc. Note that functionality of the software modules 38A-48A, similar to those described for the wearable device 16, may be combined in some embodiments, or further distributed among additional modules. In some embodiments, the execution of the application software 36A and associated modules 38A-48A may be distributed among plural devices, as set forth above.

Figure 6:
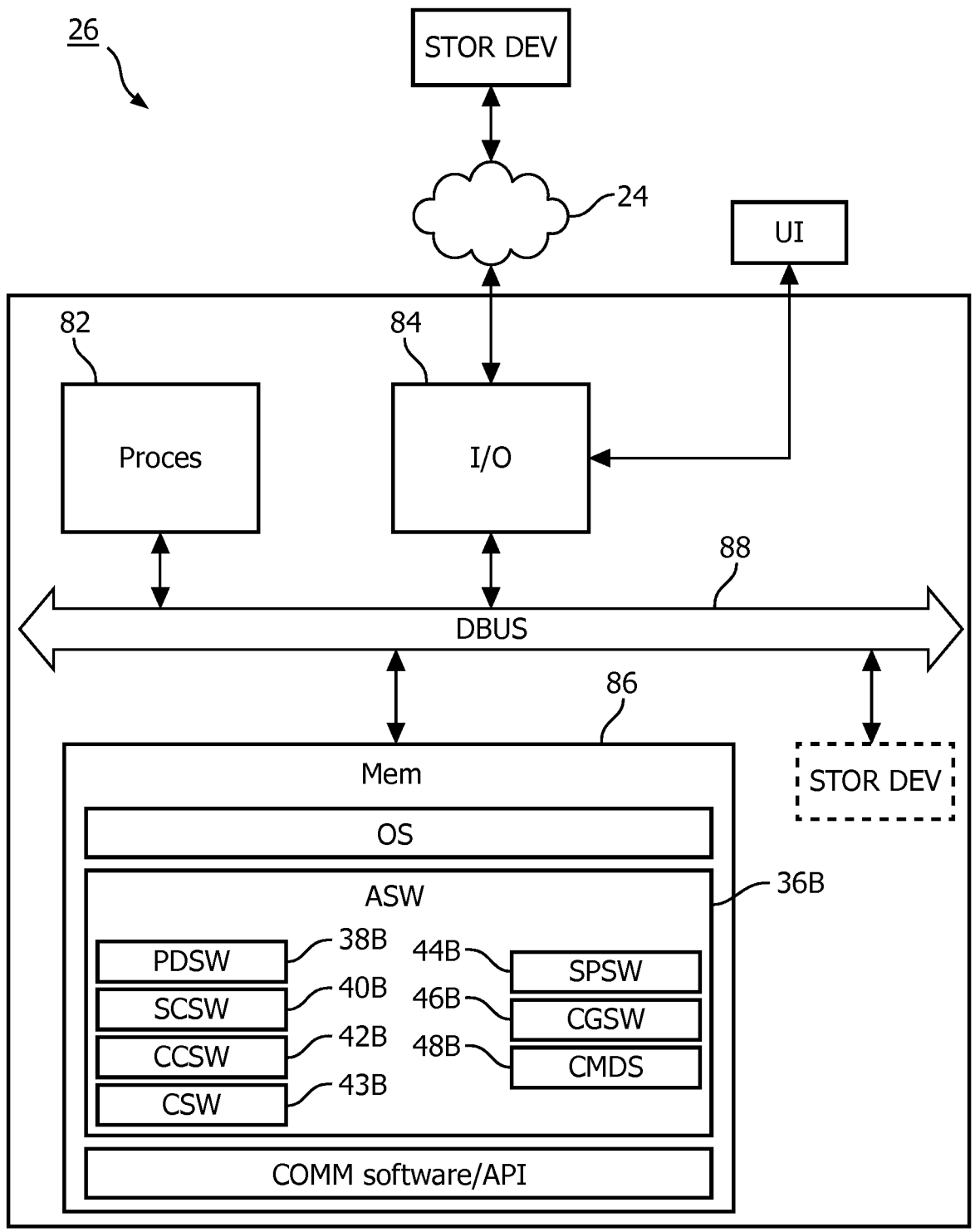
FIG. 6 is a schematic diagram that illustrates a computing system in which all or a portion of the functionality of a geometric evaluation system may be implemented, in accordance with an embodiment of the invention.

Referring now to FIG. 6, shown is a computing system 26 in which all or a portion of the functionality of a geometric evaluation system may be implemented. The computing system 26 may comprise a single computing device as shown here, or in some embodiments, may comprise plural devices that collectively perform the functionality described below. In one embodiment, the computing system 26 may be embodied as an application server, computer, among other computing devices, and is also generally referred to herein as an apparatus. One having ordinary skill in the art should appreciate in the context of the present disclosure that the example computing system 26 is merely illustrative of one embodiment, and that some embodiments of computing devices may comprise fewer or additional components, and/or some of the functionality associated with the various components depicted in FIG. 6 may be combined, or further distributed among additional modules or computing devices, in some embodiments. The computing system 26 is depicted in this example as a computer system, such as one providing a function of an application server. It should be appreciated that certain well-known components of computer systems are omitted here to avoid obfuscating relevant features of the computing system 26. In one embodiment, the computing system 26 comprises one or more processors, such as processor 82 (PROCES), input/output (I/O) interface(s) 84 (I/O), which in one embodiment is optionally coupled to a user interface (e.g., keyboard, mouse, microphone, display screen, etc.), and memory 86 (MEM), all coupled to one or more data busses, such as data bus 88 (DBUS). In some embodiments, the user interface (UI) may be coupled directly to the data bus 88. The memory 86 may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 86 may store a native operating system, one or more native applications, emulation systems, or emulated applications for any of a variety of operating systems and/or emulated hardware platforms, emulated operating systems, etc. In some embodiments, a separate storage device (STOR DEV) may be coupled to the data bus 88 or as a network-connected device (or devices) via the I/O interfaces 84 and the Internet 24. The storage device may be embodied as persistent memory (e.g., optical, magnetic, and/or semiconductor memory and associated drives) to store user data, geographical locations/maps, and/or contextual messages (e.g., the storage device may incorporate the contextual message data structure 48).

In the embodiment depicted in FIG. 6, the memory 86 comprises an operating system (OS) and the application software 36B, including all or a portion of the component parts 38B-48B). The memory 86 may comprise additional software, including software that enables communications (comm software) among network-connected devices and that provides web and/or cloud services, among other software such as one or more APIs. As the application software 36B and components software modules 38B-48B comprise the functionality of the application software 36 and modules 38-48 described above in association with the wearable device 16, discussion of the same is omitted here for brevity. It is noted that all or a portion of the functionality of the application software 36B may be implemented in the computing system 26. For instance, the computing system 26 may receive sensor data from the wearable device 16 and/or the electronics device 18, implement the software of the modules 38B-48B, and provide feedback (e.g., contextual messages) to the wearable device 16 and/or the electronics device 18. In some embodiments, the computing system 26 may only receive the plural parameters (e.g., area, area equivalent, length) from the wearable device 16 (and/or the electronics device 18), and compute the score based on the plural parameters, access internally (or in a networked-storage device) the contextual message data structure 48, and return to the wearable device 16 and/or the electronics device 18 the contextual message for presentation at the wearable device 16 and/or the electronics device 18. By handling all or at least a portion of the computations, the power requirements of the electronics device 18 and/or wearable device 16 may be reduced. Further, by handling the storage of contextual messages at the computing system 26, memory requirements at the electronics device 18 and/or the wearable device 16 are reduced. Note that in some embodiments, functionality of two or more of the modules 38B-48B may be combined into a single module, or distributed among different modules in the same or different location.

Execution of the application software 36B (and associated modules 38B-48B) may be implemented by the processor 82 under the management and/or control of the operating system. The processor 82 may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the computing system 26.

The I/O interfaces 84 comprise hardware and/or software to provide one or more interfaces to the Internet 24, as well as to other devices such as the user interfaces. In other words, the I/O interfaces 84 may comprise any number of interfaces for the input and output of signals (e.g., analog or digital data) for conveyance of information (e.g., data) over various networks and according to various protocols and/or standards. The user interfaces may include a keyboard, mouse, microphone, immersive head set, display screen, etc., which enable input and/or output by an administrator or other user.

When certain embodiments of the computing system 26 are implemented at least in part with software (including firmware), as depicted in FIG. 6, it should be noted that the software (e.g., such as the application software 36B and modules 38B-48B) can be stored on a variety of non-transitory computer-readable medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing system 26 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), relays, contactors, etc.

Figure 7A:
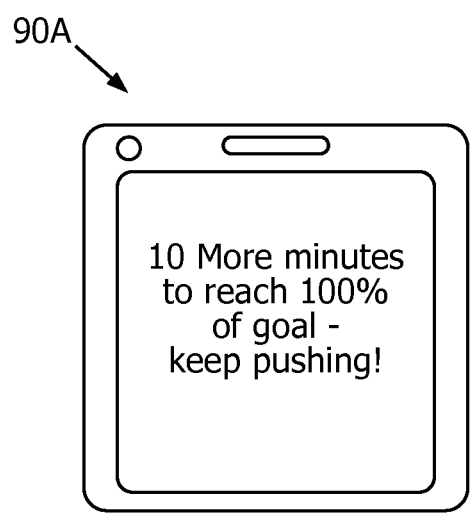
FIGS. 7A-7B are screen diagrams that illustrate example contextual messages presented to a user by a geometric evaluation system in accordance with an embodiment of the invention.
Figure 7B:
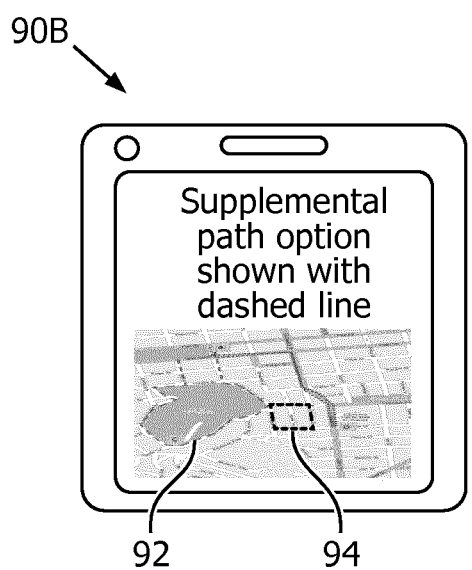

FIGS. 7A-7B are screen diagrams that illustrate example contextual messages presented to a user by a geometric evaluation system. As set forth above, the contextual messages may be presented at the wearable device 16 (e.g., at a display screen of the wearable device 16) and/or at the electronics device 18. It should be appreciated within the context of the present disclosure that the example screen diagrams are merely illustrative, and that their layout and/or contextual message may be different in some embodiments. Referring to FIG. 7A, shown is an example user interface 90A that presents visually to the user the contextual message, "10 more minutes to reach 100% of your goal—keep pushing!" Additional data may also be displayed or prompted by a user, such as physiological parameters (e.g., hear rate, calories, etc.). For instance, the user may be trying to achieve a goal of reducing weight or improving running distance. The geometric evaluation system (e.g., the application software 36, 36A, or 36B) records the location data and/or movement data and classifies the activity as health-related. Further, based on recorded goal data and the recorded sensor data indicating the distance (and/or used to derive the caloric requirements according to user data on current weight and estimated caloric loss from the current running speed), the geometric evaluation system accesses the appropriate entry among a plurality of contextual message entries from contextual message data structure 48 and conveys the contextual message presented in FIG. 7A. As noted previously, the contextual message may include feedback that encourages continued healthy behavior, informs the user of progress towards user and/or institutional targets/goals, and/or informs the user of the impact of the activity from a physiological standpoint (e.g., increased endurance, etc.).

As another example, FIG. 7B illustrates a user interface 90B that presents the contextual message, "Supplemental path option shown with dashed line." In other words, the geometric evaluation system (e.g., the application software 36, 36A, or 36B) may determine that the score is low (e.g., is utilitarian, or classified as health-related yet insufficient relative to current targets/goals), and hence triggers the supplemental path software 44 (or 44A, 44B) to determine a supplemental path that will increase the user activity. As shown, the contextual message is presented in conjunction with an image (or graphic of the same) showing the current path 92 and the suggested supplemental path 94 in conjunction with the message. Additional or different data may also be presented, such as physiological parameters, percentage toward goal, etc. Note that the conditions leading to the triggering of the supplemental path may include other and/or additional conditions than those described above, including a deficiency in meeting a particular activity goal, detected BMI, among other triggering conditions. Also, the supplemental path may cause the previously classified utilitarian path to be converted to a health-related classification. Also, though FIG. 7B shows a map, in some embodiments, the supplemental path may be presented without the use or need of a map and/or place identification.

Figure 8:
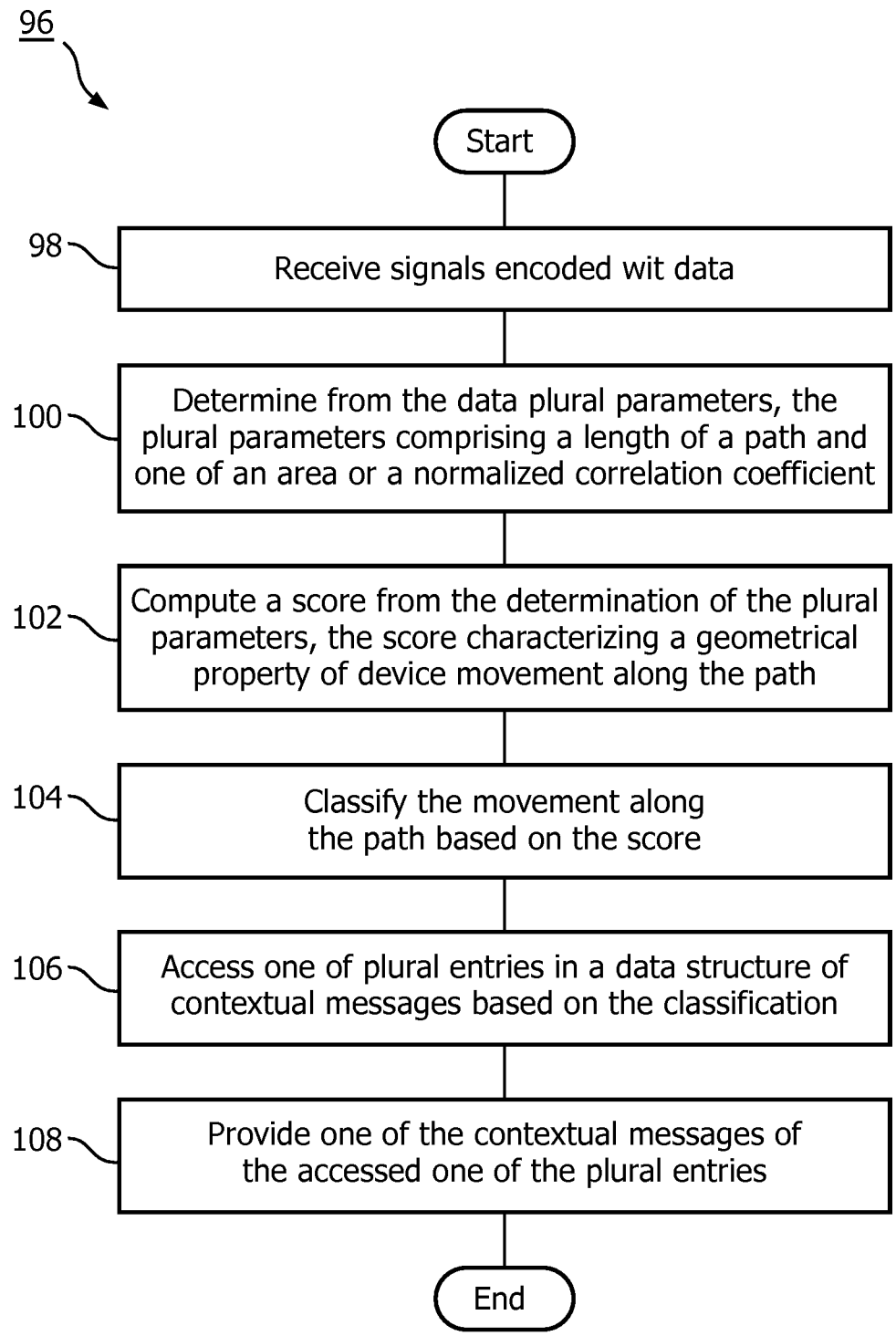
FIG. 8 is a flow diagram that illustrates an example geometric evaluation method in accordance with an embodiment of the invention.

In view of the description above, it should be appreciated that one embodiment of a geometric evaluation method, depicted in FIG. 8 and referred to as a method 96 and encompassed between start and end designations, comprises receiving signals encoded with data (98); determining from the data plural parameters, the plural parameters comprising a length of a path and one of an area or a normalized correlation coefficient (100); computing a score from the determination of the plural parameters, the score characterizing a geometrical property of device movement along the path (102); classifying the movement along the path based on the score (104); accessing one of plural entries in a data structure of contextual messages based on the classification (106); and providing one of the contextual messages of the accessed one of the plural entries (108).

Any process descriptions or blocks in the flow diagram of FIG. 8 should be understood as representing modules, segments, or portions of code which include one or more executable instructions for implementing specific logical functions or steps in the process, and alternate implementations are included within the scope of an embodiment of the present invention in which functions may be executed substantially concurrently, and/or additional logical functions or steps may be added, depending on the functionality involved, as would be understood by those reasonably skilled in the art of the present invention.

In one embodiment, a claim to an apparatus is disclosed, comprising: a user interface; plural sensors, wherein at least one of the sensors monitors movement of the apparatus; a memory comprising: a data structure having plural entries that store respective contextual messages; and application software; and a processor configured to execute the application software to: receive signals encoded with data from one or more of the plural sensors during movement of the apparatus along a path; determine from the data plural parameters, the plural parameters comprising a length of the path and one of an area or a normalized correlation coefficient; compute a score from the determination of the plural parameters, the score characterizing a geometrical property of the movement along the path; classify the movement along the path based on the score; access one of the plural entries based on the classification; and cause a presentation of one of the contextual messages of the accessed one of the plural entries via the user interface.

In one embodiment, a claim depending on the preceding claim, wherein the processor is configured to execute the application software to: compute the score based on a ratio of the area and the square of the length; and classify the movement as either utilitarian or health-related, the classification based on comparing the score with a predetermined value.

In one embodiment, a claim depending on any one of the preceding claims, wherein the processor is further configured to execute the application software to track instances of repeated movement of the apparatus along a particular path, the processor further configured to execute the application software to determine that the repeated movement corresponds to recurring healthy behavior, the processor further configured to execute the application software to perform one or more of the following: cause presentation of a contextual message that encourages the user to perform the healthy behavior more often; and cause presentation of a contextual message that informs the user about a contribution of the healthy behavior to one or a combination of health behavior targets or predicted physiological benefits.

In one embodiment, a claim depending on any one of the preceding claims, wherein the processor is configured to execute the application software to cause presentation of a contextual message that encourages a user to increase activity, the contextual message inherently intended to increase the score.

In one embodiment, a claim depending on any one of the preceding claims, wherein the processor is further configured to execute the application software to, based further on at least the score: determine one or more supplemental paths; access one of the plural entries for one of the contextual messages associated with the one or more supplemental paths; and present via the user interface the one of the accessed contextual messages associated with the one or more supplemental paths.

In one embodiment, a claim depending on any one of the preceding claims, wherein the at least one of the sensors comprises a location tracking device, and wherein, prior to the determination of the plural parameters, the processor is further configured to execute the application software to: identify recurring locations for the apparatus; sample a plurality of coordinates using the location tracking device for a plurality of paths associated with the movement of the apparatus to and from the recurring locations; and determine a type of activity associated with the movement of the apparatus for each of the plurality of paths.

In one embodiment, a claim depending on any one of the preceding claims, wherein the processor is further configured to identify the recurring locations based on a frequency in which the apparatus is determined to be located at a particular location.

In one embodiment, a claim depending on any one of the preceding claims, wherein the processor is further configured to execute the application software to restrict the determination of the plural parameters to apparatus movement where there is an associated threshold level of sensed physical activity of a user received from the plural sensors.

For instance, as described above, the user may be sitting in a vehicle in one segment, and this is the type of activity that the geometric evaluation system may exempt from further processing, choosing to process activity where the user is actually engaged in some sort of physical activity.

In one embodiment, a claim depending on any one of the preceding claims, wherein the processor is further configured to: determine a cognitive state of a user based on the score; access one of the plural entries for one of the contextual messages based on the determination of the cognitive state; and present the one of the accessed contextual messages that is based on the determination of the cognitive state via the user interface.

In one embodiment, a claim depending on any one of the preceding claims, wherein the at least one of the sensors comprises a motion tracking device, and wherein, prior to the determination of the plural parameters, the processor is further configured to execute the application software to: identify a pattern of recurring locations for the apparatus; identify a pattern of movement of the apparatus along a plurality of paths to and from the recurring locations; determine a type of activity associated with the movement of the apparatus for each of a plurality of paths; and restrict the determination of the plural parameters to apparatus movement where there is an associated threshold level of sensed physical activity of a user received from the plural sensors.

In one embodiment, a claim depending on any one of the preceding claims, wherein the processor is further configured to execute the application software to determine the plural parameters, wherein the plural parameters comprises the equivalent to the area, by: determining a normalized correlation coefficient based on motion data from the motion tracking device and additional data from the plural sensors for movement of the apparatus to and from one of the identified recurring locations, the normalized correlation coefficient characterizing a similarity of the paths to and from the identified recurring locations; and computing the score based on a combination of the normalized correlation coefficient and the length.

In one embodiment, a claim to a system is disclosed, comprising: a memory comprising: a data structure having plural entries that store respective contextual messages; and application software; and a processor configured to execute the application software to: receive signals encoded with data; determine from the data plural parameters, the plural parameters comprising a length of a path and one of an area or a normalized correlation coefficient; compute a score from the determination of the plural parameters, the score characterizing a geometrical property of device movement along the path; classify the movement along the path based on the score; access one of the plural entries based on the classification; and provide one of the contextual messages of the accessed one of the plural entries.

In one embodiment, a claim depending on the preceding system claim, wherein the processor is configured to execute the application software to: compute the score based on a ratio of the area and the square of the length; and classify the movement as either utilitarian or health-related, wherein the classification is based on comparing the score with a predetermined value.

In one embodiment, a claim depending on any one of the preceding system claims, wherein the processor is further configured to execute the application software to, based further on at least the score: determine one or more supplemental paths; access one of the plural entries for one of the contextual messages associated with the one or more supplemental paths; and provide the one of the accessed contextual messages associated with the one or more supplemental paths.

In one embodiments, a claim depending on any one of the preceding system claims, wherein the processor is further configured to execute the application software to track instances of repeated movement of a remote device along a particular path, the processor further configured to execute the application software to determine that the repeated movement corresponds to recurring healthy behavior of a user, the processor further configured to execute the application software to perform one or more of the following: provide a contextual message that encourages the user to perform the healthy behavior more often; and provide a contextual message that informs the user about a contribution of the healthy behavior to one or a combination of health behavior targets or predicted physiological benefits.

In one embodiment, a claim depending on any one of the preceding claims, wherein the processor is configured to execute the application software to provide a contextual message that encourages a user to increase activity, the contextual message inherently intended to increase the score.

In one embodiment, a claim depending on any one of the preceding system claims, wherein the data comprises location coordinates, and wherein, prior to the determination of the plural parameters, the processor is further configured to execute the application software to: identify recurring locations for a remote device based on frequency in which the remote device is determined to be located at a particular location; sample the location coordinates corresponding to movement of the remote device to and from the recurring locations; determine a type of activity associated with the movement of the remote device for each of a plurality of paths; and restrict the determination of the plural parameters to device movement where there is an associated threshold level of sensed physical activity of a user determined from the received signals.

In one embodiment, a claim depending on any one of the preceding system claims, wherein the processor is further configured to: determine a cognitive state of a user based on the score; access one of the plural entries for one of the contextual messages based on the determination of the cognitive state; and provide the one of the accessed contextual messages that is based on the determination of the cognitive state to the user.

In one embodiment, a claim depending on any one of the preceding system claims, wherein the data comprises motion tracking data, and wherein, prior to the determination of the plural parameters, the processor is further configured to execute the application software to, based on the motion tracking data: identify a pattern of recurring locations for a remote device; identify a pattern of a plurality of paths associated with movement of the remote device to and from the recurring locations; determine a type of activity associated with the movement of the remote device for each of the plurality of paths; and restrict the determination of the plural parameters to remote device movement where there is an associated threshold level of sensed physical activity of a user associated with the remote device.

In one embodiment, a claim depending on any one of the preceding system claims, wherein the processor is further configured to execute the application software to determine the plural parameters, wherein the plural parameters comprise the equivalent to the area, by: determining a normalized correlation coefficient based on the motion tracking data and additional data to and from one of the identified recurring locations, the normalized correlation coefficient characterizing a similarity of the paths to and from the identified recurring locations; and computing the score based on a combination of the normalized correlation coefficient and the length.

In one embodiment, a claim to a method is disclosed, the method comprising receiving signals encoded with data; determining from the data plural parameters, the plural parameters comprising a length of a path and one of an area or a normalized correlation coefficient; computing a score from the determination of the plural parameters, the score characterizing a geometrical property of device movement along the path; classifying the movement along the path based on the score; accessing one of plural entries in a data structure of contextual messages based on the classification; and providing one of the contextual messages of the accessed one of the plural entries.

In one embodiment, a claim depending on the preceding method claim, wherein the providing comprises presenting the contextual message on a user interface.

While the invention has been illustrated and described in detail in the drawings and foregoing description, such illustration and description are to be considered illustrative or exemplary and not restrictive; the invention is not limited to the disclosed embodiments. For example, the geometric evaluation system, though described as an alternative to existing context-based activity monitoring systems, may be used in conjunction with such systems in some embodiments to improve accuracy. For instance, a first stage in classifying the activity may be based on the geometric evaluation system, and the existing systems may be used in a second stage to corroborate the results of the geometric evaluation systems (or vice versa). For instance, a path on which a user runs or walks may be traversed in both directions (e.g., a straight-line path), which may result in a low score despite being health-related, and a classification as utilitarian. Physiological sensors may be used to detect a physiological parameter, such as heart rate, and if the heart rate exceeds a predetermined threshold, the classification as utilitarian may be overruled by the second stage of physiological sensing. Other variations to the disclosed embodiments can be understood and effected by those skilled in the art in practicing the claimed invention, from a study of the drawings, the disclosure, and the appended claims. Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

The invention claimed is:

1. A system, comprising:
 a memory comprising:
  a data structure having plural entries that store respective contextual messages; and
  application software; and
 at least one processor configured to execute the application software to:
  receive signals encoded with data from one or more of plural sensors of a user apparatus during movement of the user apparatus along an ambulatory path;
  determine, from the data, plural parameters, the plural parameters comprising a length of the path, and at least one of: an area enclosed by the path and a normalized correlation coefficient, the normalized correlation coefficient characterizing a similarity of the paths to and from identified recurring locations;
  compute a score from the plural parameters, the score characterizing a geometrical property of the movement along the path;
  classify the movement along the path based on the score;
  access one of the plural entries based on the classification; and
  cause a presentation to the user of one of the contextual messages of the accessed one of the plural entries via the user interface.

2. The system of claim 1, wherein the processor is configured to execute the application software to:
 compute the score based on a ratio of the area and a square of the length; and
 classify the movement as either utilitarian or health-related with respect to the user, the classification based on comparing the score with a predetermined value.

3. The system of claim 2, wherein the processor is further configured to execute the application software to track instances of repeated movement of the apparatus along a particular path, the processor further configured to execute the application software to determine that the repeated movement corresponds to recurring healthy behavior, the processor further configured to execute the application software to perform one or more of the following:
 cause presentation of a contextual message that encourages the user to perform the healthy behavior more often; and
 cause presentation of a contextual message that informs the user about a contribution of the healthy behavior to one or a combination of health behavior targets or predicted physiological benefits.

4. The system of claim 2, wherein the processor is configured to execute the application software to cause presentation of a contextual message that encourages a user to increase activity, the contextual message inherently intended to increase the score.

5. The system of claim 2, wherein the processor is further configured to execute the application software to, based further on at least the score:
 determine one or more supplemental paths;
 access one of the plural entries for one of the contextual messages associated with the one or more supplemental paths; and
 present via the user interface the one of the accessed contextual messages associated with the one or more supplemental paths.

6. The system of claim 1, wherein the at least one of the sensors comprises a location tracking device, and wherein, prior to the determination of the plural parameters, the processor is further configured to execute the application software to:

identify recurring locations for the apparatus;
sample a plurality of coordinates using the location tracking device for a plurality of paths associated with the movement of the apparatus to and from the recurring locations; and
determine a type of activity associated with the movement of the apparatus for each of the plurality of paths.

7. The system of claim 6, wherein the processor is further configured to identify the recurring locations based on a frequency in which the apparatus is determined to be located at a particular location.

8. The system of claim 6, wherein the processor is further configured to execute the application software to restrict the determination of the plural parameters to apparatus movement where there is an associated threshold level of sensed physical activity of a user received from the plural sensors.

9. The system of claim 1, wherein the processor is further configured to:
determine a cognitive state of a user based on the score;
access one of the plural entries for one of the contextual messages based on the determination of the cognitive state; and
present the one of the accessed contextual messages that is based on the determination of the cognitive state via the user interface.

10. The system of claim 1, wherein the at least one of the sensors comprises a motion tracking device, and wherein, prior to the determination of the plural parameters, the processor is further configured to execute the application software to:
identify a pattern of recurring locations for the apparatus;
identify a pattern of movement of the apparatus along a plurality of paths to and from the recurring locations;
determine a type of activity associated with the movement of the apparatus for each of a plurality of paths; and
restrict the determination of the plural parameters to apparatus movement where there is an associated threshold level of sensed physical activity of a user received from the plural sensors.

11. The system of claim 10, wherein the plural parameters comprises the equivalent to the area, by determining the normalized correlation coefficient based on motion data from the motion tracking device and additional data from the plural sensors for movement of the apparatus to and from one of the identified recurring locations, and
wherein the score is based on a combination of the normalized correlation coefficient and the length.

12. The system of claim 1, further comprising the user apparatus comprising a user interface and the plural sensors, wherein at least one of the sensors monitors the ambulatory movement of the user apparatus.

13. A method, comprising:
receiving signals encoded with data;
determining, from the data, plural parameters, the plural parameters comprising a length of an ambulatory path of a user and at least one of: an area enclosed by the path and a normalized correlation coefficient, the normalized correlation coefficient characterizing a similarity of paths to and from identified recurring locations;
computing a score from the plural parameters, the score characterizing a geometrical property of device movement along the path;
classifying the movement along the path based on the score;
accessing one of plural entries in a data structure of contextual messages based on the classification; and
providing to the user one of the contextual messages of the accessed one of the plural entries.

14. The method of claim 13, further comprising:
computing the score based on a ratio of the area and a square of the length; and
classifying the movement as either utilitarian or health-related with respect to the user, the classification based on comparing the score with a predetermined value.

15. The method of claim 13, further comprising:
tracking instances of repeated movement of the apparatus along a particular path;
determining that the repeated movement corresponds to recurring healthy behavior;
causing presentation of a contextual message that encourages the user to perform the healthy behavior more often; and
causing presentation of a contextual message that informs the user about a contribution of the healthy behavior to one or a combination of health behavior targets or predicted physiological benefits.

16. The method of claim 13, further comprising:
identifying recurring locations based on a frequency in which the apparatus is determined to be located at a particular location.

17. The method of claim 13, further comprising:
determining one or more supplemental paths;
accessing one of the plural entries for one of the contextual messages associated with the one or more supplemental paths; and
presenting via the user interface the one of the accessed contextual messages associated with the one or more supplemental paths.

18. The method of claim 13, further comprising:
restricting the determination of the plural parameters to apparatus movement where there is an associated threshold level of sensed physical activity of a user received from the plural sensors.

* * * * *